United States Patent
Kim et al.

(10) Patent No.: US 12,350,272 B2
(45) Date of Patent: Jul. 8, 2025

(54) PYRIDOPYRIMIDINONE DERIVATIVES FOR USE AS AXL INHIBITORS

(71) Applicant: OSCOTEC INC., Seongnam-si (KR)

(72) Inventors: Jung-Ho Kim, Seongnam-si (KR); Jang-Sik Choi, Cheonan-si (KR); Hee Kyu Lee, Suwon-si (KR); Dong-Sik Jung, Cheonan-si (KR); Sung-Ho Park, Siheung-si (KR); Yung-Geun Choi, Suwon-si (KR)

(73) Assignee: OSCOTEC INC., Seongnam-si (KR)

( * ) Notice: Subject to any disclaimer, the term of this patent is extended or adjusted under 35 U.S.C. 154(b) by 732 days.

(21) Appl. No.: 17/255,589

(22) PCT Filed: Jun. 26, 2019

(86) PCT No.: PCT/KR2019/007733
§ 371 (c)(1),
(2) Date: Dec. 23, 2020

(87) PCT Pub. No.: WO2020/004938
PCT Pub. Date: Jan. 2, 2020

(65) Prior Publication Data
US 2021/0275532 A1    Sep. 9, 2021

Related U.S. Application Data

(60) Provisional application No. 62/690,620, filed on Jun. 27, 2018.

(51) Int. Cl.
*A61K 31/519* (2006.01)
*A61K 39/00* (2006.01)
(Continued)

(52) U.S. Cl.
CPC ........ *A61K 31/519* (2013.01); *A61K 39/3955* (2013.01); *A61P 35/00* (2018.01); *A61P 35/02* (2018.01); *A61K 2039/505* (2013.01)

(58) Field of Classification Search
CPC combination set(s) only.
See application file for complete search history.

(56) References Cited

U.S. PATENT DOCUMENTS

2013/0274274 A1    10/2013    Kim et al.
2015/0232470 A1    8/2015    Whitlock et al.

FOREIGN PATENT DOCUMENTS

WO    99/19774 A1    4/1999
WO    99/35146 A1    7/1999
(Continued)

OTHER PUBLICATIONS

Myers SH, Brunton VG, Unciti-Broceta A. AXL Inhibitors in Cancer: A Medicinal Chemistry Perspective. J Med Chem. Apr. 28, 2016; 59(8):3593-608. doi: 10.1021/acs.jmedchem.5b01273. Epub Nov. 20, 2015. PMID: 26555154. (Year: 2015).*
(Continued)

*Primary Examiner* — Adam Weidner
*Assistant Examiner* — Laura Ann Essex
(74) *Attorney, Agent, or Firm* — Sughrue Mion, PLLC

(57) ABSTRACT

Pyridopyrimidinone derivatives and pharmaceutical compositions containing the same for use as an Axl inhibitor for the treatment of a disease or condition mediated by Axl such as cancer and metastasis, are disclosed. Also disclosed are methods for treating a Axl-mediated disease or condition by administering to a subject a therapeutically effective amount of the pyridopyrimidinone derivative.

5 Claims, 14 Drawing Sheets

(51) Int. Cl.
  A61K 39/395    (2006.01)
  A61P 35/00     (2006.01)
  A61P 35/02     (2006.01)

(56) References Cited

FOREIGN PATENT DOCUMENTS

| WO | WO-2011053861 A1 * | 5/2011 | ........... A61K 31/519 |
| WO | 2013/142382 A1 | 9/2013 | |
| WO | 2016/193680 A1 | 12/2016 | |
| WO | WO-2017059280 A1 * | 4/2017 | ........... A61K 31/506 |

OTHER PUBLICATIONS

Lee et al., "G-749, a novel FLT3 kinase inhibitor, can overcome drug resistance for the treatment of acute myeloid leukemia", Blood, Apr. 3, 2014, vol. 123, No. 14, pp. 2209-2219 (11 pages).
Feneyrolles et al., "Axl Kinase as a Key Target for Oncology: Focus on Small Molecule Inhibitors", Mol Cancer Ther, 2014, vol. 13, No. 9, pp. 2141-2148 (8 pages).
Myers et al., "AXL Inhibitors in Cancer: A Medicinal Chemistry Perspective", Journal of Medicinal Chemistry, 2016, vol. 59, pp. 3593-3608 (16 pages).
Erinn B. Rankin et al., "The Receptor Tyrosine Kinase AXL in Cancer Progression", Cancers, 2016, pp. 1-16, 8, 103.
International Searching Authority, Written Opinion for PCT/KR2019/007733, dated Oct. 1, 2019.
International Searching Authority, International Search Report for PCT/KR2019/007733, dated Oct. 1, 2019.
Hsin-Jung Lee et al., "Gas6/Axl pathway promotes tumor invasion through the transcriptional activation of Slug in hepatocellular carcinoma", Carcinogenesis, vol. 35, No. 4, 2014 , pp. 769775 (7 pages total) (online publication Nov. 14, 2013).
Ines Hasanbasic et al., "Intracellular signaling pathways involved in Gas6-Axl-mediated survival of endothelial cells", Am J Physiol Heart Circ Physiol, vol. 287, May 6, 2004, pp. H1207-H1213 (7 pages total).
Wei-Ping Lee et al., "Akt is required for Axl-Gas6 signaling to protect cells from E1A-mediated Apoptosis", Oncogene, vol. 21, 2002, pp. 329 336 (8 pages).
Georgina Collet et al., "Receptor Tyrosine Kinase Axl Modulates the Osteogenic Differentiation of Pericytes", Circulation Research, vol. 92, 2003, pp. 1123-1129 (8 pages total).
Yun Jung Choi et al., "AXL and MET receptor tyrosine kinases are essential for lung cancer metastasis", Oncology Reports, vol. 37, 2017, pp. 2201-2208 (8 pages total).
Guoan Zhang et al., "Function of Axl receptor tyrosine kinase in non-small cell lung cancer (Review)", Oncology Letters, vol. 15, 2018, pp. 2726-2734 (9 page total).
Timothy M. Dalfonso et al., "Axl receptor tyrosine kinase expression in breast cancer", Clinical Pathology, published online Jun. 5, 2014, pp. 1-7 (8 pages total).
Gaoyuan Jin et al., "Expression of Axl and its prognostic significance in human breast cancer", Oncology Letters, vol. 13, 2017, pp. 621-628 (8 pages total).
H Yu et al., "Axl receptor tyrosine kinase is a potential therapeutic target in renal cell carcinoma", British Journal of Cancer, published online Jul. 16, 2015, pp. 1-10 (10 pages total).
L Zhou et al., "Targeting MET and AXL overcomes resistance to sunitinib therapy in renal cell carcinoma", Oncogene, 2015, pp. 1-11 (11 pages total).
Xiaoliang Wu et al., "AXLGAS6 expression can predict for adverse prognosis in nonsmall cell lung cancer with brain metastases", Journal of Cancer Research and Clinical Oncology, published online May 27, 2017, published on line, 17 pages total.
Luis Eduardo Zucca et al., "Expression of tyrosine kinase receptor AXL is associated with worse outcome of metastatic renal cell carcinomas treated with sunitinib", Urologic Oncology, 2017, pp. 1-8 (9 pages total).
Toni M. Brand et al., "AXL Is a Logical Molecular Target in Head and Neck Squamous Cell Carcinoma", Clinical Cancer Research, Published online Mar. 12, 2015, published online, (14 pages total).
Colinda L.G.J. Scheele et al., "Intravital Insights into Heterogeneity, Metastasis, and Therapy Responses", Cell Press, 2016, pp. 1-10 (12 pages total).
Jane Antony et al., "AXL-Driven EMT State as a Targetable Conduit in Cancer", Cancer Research, vol. 77(14), published online Jun. 30, 2017, pp. OF1-OF8, (9 pages total).
Fang Wu et al., "The role of Axl in drug resistance and epithelial-to-mesenchymal transition of non-small cell lung carcinoma", Int J Clin Exp Pathol, Oct. 1, 2014, 2014, vol. 7(10), pp. 6653-6661 (9 pages total).
K-Y Tai et al., "Axl promotes cell invasion by inducing MMP-9 activity through activation of NF-κB and Brg-1", Oncogene, Mar. 17, 2008, vol. 27, pp. 4044-4055 (12 pages total).
Todd A. Aguilera et al., "Reprogramming the immunological microenvironment through radiation and targeting Axl", Nature Communications, Dec. 23, 2016, vol. 7:13898, pp. 1-14 (14 pages total).
Paul Elvin et al., "Tumour invasion and metastasis: challenges facing drug discovery", Current Opinion in Pharmacology, Jun. 13, 2005, vol. 5, pp. 374-381 (8 pages total).
Manikandan Subramanian et al., "An AXL/LRP-1/RANBP9 complex mediates DC efferocytosis and antigen cross-presentation in vivo", The Journal of Clinical Investigation, Mar. 2014, vol. 124, No. 3, pp. 1296-1308 (13 pages total).
Heath D. Skinner et al., "Integrative Analysis Identifies a Novel AXLPI3 KinasePD-L1 Signaling Axis Associated with Radiation Resistance in Head and Neck Cancer", Clinical Cancer Research, May 5, 2017, published online, pp. OF1-OF10 (11 pages total).
Willy Hugo et al., "Genomic and Transcriptomic Features of Response to Anti-PD-1 Therapy in Metastatic Melanoma", Cell Press, Mar. 24, 2016, vol. 165, pp. 35-44 (11 pages total).
Nicholas L. Syn et al., "De-novo and acquired resistance to immune checkpoint targeting", Lancet Oncology, Dec. 2017, vol. 18: pp. e731-e741 (11 pages total).
Shengyu Yang et al., "Mouse Models for Tumor Metastasis", Rational Drug Design: Methods and Protocols, Methods in Molecular Biology, 2012, vol. 928, pp. 221-227 (8 pages total).
John Reiser et al., "Effector, Memory, and Dysfunctional CD8+ T Cell Fates in the Antitumor Immune Response", Journal of Immunology Research, 2016, pp. 1-14 (15 pages total).
Jing Liu et al., "Improved Efficacy of Neoadjuvant Compared to Adjuvant Immunotherapy to Eradicate Metastatic Disease", Cancer Discovery, published online Sep. 23, 2016, published online, pp. 1382-1399 (19 pages total).
Douglas K. Graham et al., "The TAM family: phosphatidylserine-sensing receptor tyrosine kinases gone awry in cancer", Nature Reviews, Dec. 2014, vol. 14, pp. 769-785 (17 pages total).
Chenjing Zhu et al., "AXL receptor tyrosine kinase as a promising anti-cancer approach: functions, molecular mechanisms and clinical applications", Molecular Cancer, published online Nov. 4, 2019, vol. 18:153, pp. 1-22 (22 pages total).
Marlies J.W. Peeters et al., "TAM-ing T cells in the tumor microenvironment: implications for TAM receptor targeting", Cancer Immunology, Immunotherapy, published online Oct. 29, 2019, vol. 69, pp. 237-244 (8 pages total).
Hector Peinado et al., "Pre-metastatic niches: organ-specific homes for metastases", Nature Reviews Cancer, 2017, published online Mar. 17, 2017, pp. 1-16 (16 pages total).
P. Schmid et al., "Pembrolizumab plus chemotherapy as neoadjuvant treatment of high-risk, early-stage triple-negative breast cancer: results from the phase 1b open-label, multicohort Keynote-173 study", Annals of Oncology, Feb. 14, 2020, vol. 31, issue 5, pp. 569-581 (13 pages total).
P.M. Forde et al., "Neoadjuvant PD-1 Blockade in Resectable Lung Cancer", The New England Journal of Medicine, Apr. 16, 2018, vol. 378;21, pp. 1976-1986 (11 pages total).

(56) References Cited

OTHER PUBLICATIONS

Mark G. Saulnier et al., "An Efficient Method for the Synthesis of Guanidino Prodrugs", Bioorganic & Medicinal Chemistry Letters, 1994, vol. 4, No. 16, pp. 1985-1990 (6 pages total).

* cited by examiner

CT-26 peritoneal metastasis models

Vehicle Control

| | | | | | |
|---|---|---|---|---|---|
| Day 0 | | | | | |
| Day 3 | | | | | |
| Day 6 | | | | | |
| Day 9 | Death | Death | | | |
| Day 12 | | | | | |
| Day 15 | | | | | |

PYRIDOPYRIMIDINONE DERIVATIVES FOR USE AS AXL INHIBITORS

CROSS REFERENCE TO RELATED APPLICATIONS

This application is a National Stage of International Application No. PCT/KR2019/007733 filed Jun. 26, 2019, claiming priority based on U.S. Provisional Patent Application No. 62/690,620 filed Jun. 27, 2018.

TECHNICAL FIELD

The present invention relates to pyridopyrimidinone derivatives and compositions comprising the same, which are useful as Axl inhibitors for the treatment of a disease or condition mediated by Axl.

BACKGROUND ART

Protein kinases play a central role in the regulation of a wide variety of cellular processes and maintaining control over cellular function. Protein kinases catalyze and regulate the process of phosphorylation, whereby the kinases covalently attach phosphate groups to proteins or lipid targets in response to a variety of extracellular signals. Extracellular stimuli such as hormones, neurotransmitters, growth and differentiation factors, cell cycle events, environmental stresses and nutritional stresses, may affect one or more cellular responses related to cell growth, migration, differentiation, secretion of hormones, activation of transcription factors, muscle contraction, glucose metabolism, control of protein synthesis, and regulation of the cell cycle.

Axl is a member of the TAM (Tyro3-Axl-Mer) family of receptor tyrosine kinases, which, when activated, can regulate tumor cell survival, proliferation, migration and invasion, angiogenesis, and tumor-host interactions. Overexpression of Axl has been described in multiple malignancies from epithelial and hematological origins and is often associated with poor prognosis. Moreover, Axl expression is associated with epithelial to mesenchymal transition (EMT), a frequent feature of metastatic tumors often correlated to drug resistance.

The majority of Axl signaling occurs in a ligand dependent manner mediated by growth arrest-specific 6 (GAS6). Upon GAS6 binding to Axl, Axl subsequently activates the signaling pathways downstream such as phosphoinositide 3-kinase (PI3K), RAt sarcoma (RAS), and extracellular signal regulated kinase (ERK). In cancer, Axl signaling can be activated by GAS6 in an autocrine or paracrine manner.

Clinically, Axl is highly expressed in primary tumors and metastasis in comparison to normal tissues. Immunohistochemical analysis of primary tumors revealed that Axl expression correlates with metastasis and/or poor survival in patients with lung adenocarcinoma, glioblastoma multiforme, breast, pancreatic, renal cell carcinoma, esophageal adenocarcinoma, oral squamous carcinoma, pleural mesothelioma, ovarian adenocarcinoma, colon cancer, head and neck squamous cell carcinoma, urothelial carcinoma, esophageal cell carcinoma, and hepatocellular carcinoma. Moreover, Axl expression correlates with drug resistance in patients with breast cancer, melanoma, myeloid leukemia, lung cancer, and renal cell carcinoma (see Rankin and Giaccia, Cancers, 2016, 103:1-16). Therefore, GAS6/Axl signaling as an important pathway driving tumor growth, metastasis, and drug resistance.

In addition, Axl is a key factor upregulated by tumor cells to promote resistance to multiple anti-cancer strategies including myeloid leukemia, non-small cell lung cancer, triple negative breast cancer (TNBC), esophageal, and ovarian cancer. For example, the level of Axl is highly correlates with epidermal growth factor receptor (EGFR) inhibitor resistance in non-small cell lung cancer, mitogen-activated protein kinases (MAPK) inhibitor resistance in melanoma and human EGFR type 2 (HER2) inhibition in breast cancer patients. Most importantly, genetic and therapeutic inhibition of Axl is sufficient to sensitize to these inhibitions, suggesting that Axl inhibition may improve response to anti-cancer therapies be an effective strategy to prevent and inhibit drug-resistance and recurrence in multiple cancers.

Meanwhile, PCT Publication No. WO 2013/142382 discloses 4-phenylamino-pyrido[4,3,-d]pyrimidin-5-one derivatives and their use as FLT3 inhibitors, however, it does not discloses their uses as Axl inhibitors or for the treatment of Axl-mediated diseases.

DISCLOSURE OF INVENTION

Technical Problem

The inventors of the present invention have been studying compounds that can be used as an Axl inhibitor, and have accomplished the present invention by confirming that 4-phenylamino-pyrido[4,3,-d]pyrimidin-5-one derivatives having specific structures effectively inhibit the activity of Axl receptor tyrosine kinase and thus can be effectively used for the treatment of diseases associated therewith.

Accordingly, an object of the present invention is to provide pyridopyrimidinone derivatives and compositions comprising the same, which are useful as Axl inhibitors for the treatment of a disease or condition mediated by Axl such as multiple types of cancer and metastasis.

Solution to Problem

In one aspect, the present invention provides a use of a compound represented by Formula (I) or a pharmaceutically acceptable salt thereof, as an Axl inhibitor for the treatment of a disease or condition mediated by Axl:

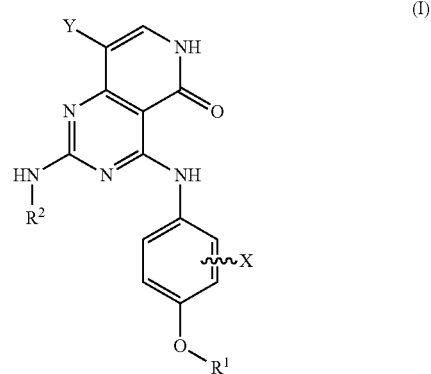

(I)

wherein
R$^1$ is C$_6$-C$_{10}$aryl, C$_6$-C$_{10}$arylC1-C$_6$alkyl, C$_5$-C$_6$cycloalkyl or C$_5$-C$_6$cycloalkylmethyl, optionally substituted with one or two R$^3$s;
R$^3$ is independently fluoro, chloro, bromo, iodo, C$_1$-C$_6$alkyl, or trifluoromethyl;

X is H, fluoro, chloro, bromo, iodo, methyl, or trifluoroethyl;

Y is chloro, bromo, iodo, $C_1$-$C_3$alkyl, or phenyl;

$R^2$ is $C_3$-$C_6$cycloalkyl or 4 to 7-membered heterocycloalkyl, wherein the $C_3$-$C_6$cycloalkyl is optionally substituted at carbon atoms with one or two $R^4$s, and wherein the 4 to 7-membered heterocycloalkyl has 1 or 2 heteroatoms selected from the group consisting of nitrogen, oxygen, sulfur, sulfone and sulfoxide, and is optionally substituted at carbon atom with $R^4$ or at nitrogen atom with $R^5$;

$R^4$ is independently hydroxy, hydroxy$C_1$-$C_6$alkyl, amino, amino$C_1$-$C_6$alkyl, —NH(—$C_1$-$C_3$alkyl), —N(—$C_1$-$C_3$alkyl)$_2$, $C_1$-$C_3$alkyl or halo; and $R^5$ is H, $C_1$-$C_3$alkyl or —C(=O)(—$C_1$-$C_3$alkyl), wherein the $C_1$-$C_3$alkyl is optionally substituted with 1 to 3 fluoros.

In another aspect, the present invention provides a use of individual stereoisomers, mixture of stereoisomers, prodrug derivatives, protected derivatives, N-oxide derivatives, solvates or hydrides of a compound of Formula (I) as defined above, as an Axl inhibitor for the treatment of a disease or condition mediated by Axl.

In another aspect, the present invention provides a use of a compound as defined above or a pharmaceutically acceptable salt thereof, for preparing a medicament for the treatment of a disease or condition mediated by Axl.

In another aspect, the present invention provides a pharmaceutical composition comprising a compound of Formula (I) as defined above or a pharmaceutically acceptable salt thereof, in combination with a pharmaceutically acceptable carrier, diluent, adjuvant or excipient.

In another aspect, the present invention provides a pharmaceutical composition comprising a compound of Formula (I) as defined above or a pharmaceutically acceptable salt thereof as an active ingredient, for the treatment of a disease or condition mediated by Axl.

In another aspect, the present invention provides a method for treating a disease or condition mediated by Axl, comprising administering to a subject in need thereof an effective amount of a compound of Formula (I) as defined above or a pharmaceutically acceptable salt thereof.

In another aspect, the present invention provides a method for inhibiting Axl receptor tyrosine kinase or for inhibiting growth of cancer cells.

Advantageous Effects of Invention

A compound of Formula (I) as defined above or a pharmaceutically acceptable salt thereof, and a pharmaceutical composition comprising the same, inhibit Axl receptor tyrosine kinase and are useful for the treatment of a disease or condition mediated by Axl, e.g., cell proliferative diseases such as multiple types of cancer and metastasis.

BEST MODE FOR CARRYING OUT THE INVENTION

Figure 1A:
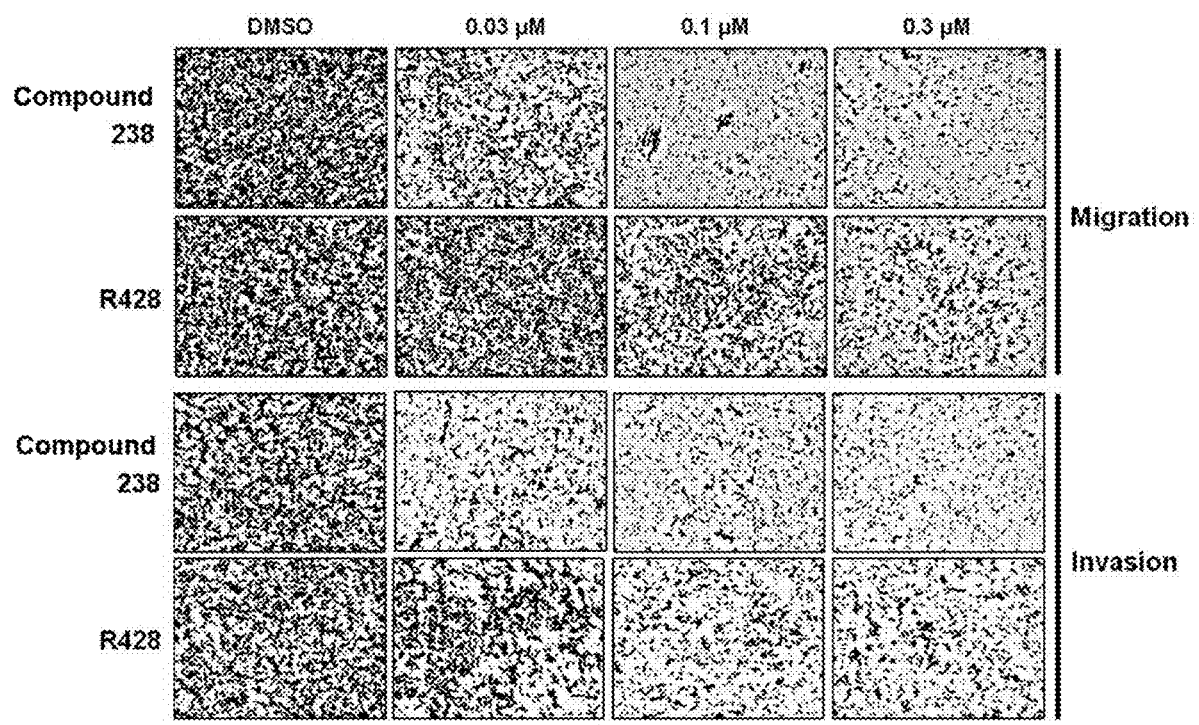
FIGS. 1a to 1c show results in migration and invasion assays of compounds 238 and R428.

Hereinafter, the present invention will be described in detail.

The term "alkyl," used alone or as part of a larger moiety such as "arylalkyl" or "cycloalkyl" refers to a straight or branched hydrocarbon radical having from 1 to 15 carbon atoms or from 1 to 8 carbon atoms (unless stated otherwise) and includes, for example, methyl, ethyl, n-propyl, i-propyl, n-butyl, sec-butyl, i-butyl, tert-butyl, n-pentyl, i-pentyl, n-hexyl and the like. An alkyl can be unsubstituted or substituted with one or more suitable substituents.

The term "cycloalkyl" refers to a monocyclic or polycyclic hydrocarbon ring group and includes, for example, cyclopropyl, cycloheptyl, cyclooctyl, cyclodecyl, cyclobutyl, adamantyl, norpinanyl, decalinyl, norbornyl, cyclohexyl, cyclopentyl, and the like. A cycloalkyl group can be unsubstituted or substituted with one or more suitable substituents.

The term "hetero" refers to the replacement of at least one carbon atom member in a ring system with at least one heteroatom such as nitrogen, sulfur, sulfone, sulfoxide and oxygen.

The term "heterocycloalkyl" means a non-aromatic monocyclic or polycyclic ring comprising carbon and hydrogen atoms and at least one heteroatom, preferably, 1 to 4 heteroatoms selected from nitrogen, sulfur, oxygen, sulfone, or sulfoxide. A heterocycloalkyl group can have one or more carbon-carbon double bonds or carbon-heteroatom double bonds in the ring group as long as the ring group is not rendered aromatic by their presence.

Examples of heterocycloalkyl groups include azetidinyl, aziridinyl, pyrrolidinyl, piperidinyl, piperazinyl, homopiperazinyl, morpholino, thiomorpholino, tetrahydrofuranyl, tetrahydrothiofuranyl, tetrahydropyranyl, pyranyl, and the like. A heterocycloalkyl group can be unsubstituted or substituted with one or more suitable substituents.

As used herein, the term "halo" includes fluoro, chloro, bromo, and iodo.

As used herein, the term "alkoxy" refers to the alkyl groups above bound through oxygen, examples of which include methoxy, ethoxy, i-propoxy, tert-butoxy, and the like. In addition, alkoxy also refers to polyethers such as —O—($CH_2$)$_2$—O—$CH_3$, and the like. An alkoxy can be unsubstituted or substituted with one or more suitable substituents.

As used herein, the term "aryl" refers to unsubstituted or substituted aromatic monocyclic or polycyclic groups and includes, for example, phenyl and naphthyl. The term "aryl" also includes a phenyl ring fused to a non-aromatic carbocyclic or heterocyclic ring. The term "aryl" may be interchangeably used with "aryl ring," "aromatic group," and "aromatic ring." Heteroaryl groups have 4 to 14 atoms, 1 to 9 of which are independently selected from the group consisting of oxygen, sulfur and nitrogen. An aryl or heteroaryl can be a mono- or bicyclic aromatic group. Typical aryl and heteroaryl groups include, for example, phenyl, quinolinyl, indazolyl, indolyl, dihydrobenzodioxynyl, 3-chlorophenyl, 2,6-dibromophenyl, pyridyl, pyrimidinyl, 3-methylpyridyl, benzothienyl, 2,4,6-tribromophenyl, 4-ethylbenzothienyl, furanyl, 3,4-diethylfuranyl, naphthyl, 4,7- dichloronaphthyl, pyrrolyl, pyrazolyl, imidazolyl, thiazolyl, and the like. An aryl or heteroaryl can be unsubstituted or substituted with one or more suitable substituents.

As used herein, the term "haloalkyl" refers to any alkyl radical having one or more hydrogen atoms replaced by a halogen atom. Examples of haloalkyl include —$CF_3$, —$CFH_2$, —$CF_2H$, and the like.

As used herein, the term "hydroxyl" or "hydroxy" refers to —OH.

As used herein, the term "amino" refers to —$NH_2$.

As used herein, the term "hydroxyalkyl" refers to any hydroxyl derivative of alkyl radical. The term "hydroxyalkyl" includes any alkyl radical having one or more hydrogen atoms replaced by a hydroxy group.

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

As described above, certain groups can be unsubstituted or substituted with one or more suitable substituents by other than hydrogen at one or more available positions, typically 1, 2, 3, 4 or 5 positions, by one or more suitable groups (which may be the same or different). Certain groups, when substituted, are substituted with 1, 2, 3 or 4 independently selected substituents. Suitable substituents include halo, alkyl, haloalkyl, aryl, hydroxy, alkoxy, hydroxyalkyl, amino, and the like.

As used herein, the term "kinase" refers to Axl. Kinase assays containing the kinases described herein are commercially available for biochemically profiling kinase inhibitors for their selectivity. In certain embodiments, a kinase is a mammalian kinase, such as a human kinase.

As used herein, the term "dermatological disorder" refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, and urticaria.

As used herein, the term "respiratory disease" refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

As used herein, the term "cancer" refers to an abnormal growth of cells which is tend to proliferate in an uncontrolled way and, in some cases, to metastasize. The types of cancer include, but are not limited to, solid tumors, such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

As used herein, the term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function, which may be partial or complete, temporary or permanent. Inflammation takes many forms and includes, but is not limited to, inflammation that is one or more of the following, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arteritis); joints (arthritis: crystalline, osteo-, psoriatic, reactive, rheumatoid, Reiter's); gastrointestinal tract; skin (dermatitis); or multiple organs and tissues (systemic lupus erythematosus).

As used herein, the term "cardiovascular disease" refers to diseases affecting the heart or blood vessels or both, including but not limited to atherosclerosis, arrhythmia, angina, myocardial ischemia, myocardial infarction, cardiac or vascular aneurysm, vasculitis, stroke, peripheral obstructive arteriopathy of a limb, an organ or a tissue, reperfusion injury following ischemia of an organ or a tissue, endotoxic, surgical or traumatic shock, hypertension, valvular heart disease, heart failure, abnormal blood pressure, vasoconstriction, vascular abnormality, or inflammation.

As used herein, the term "inhibitor" refers to a compound which inhibits one or more kinases described herein. For example, the term "Axl inhibitor" refers to a compound which inhibits the Axl receptor or reduces the signaling effect.

As used herein, the term "pharmaceutically acceptable" refers to a material, such as a carrier or diluent, which does not abrogate the biological activity or properties of the compounds described herein. Such materials are administered to an individual without causing undesirable biological effects or interacting in a deleterious manner with any of the components of the composition in which it is contained.

As used herein, the term "pharmaceutically acceptable salt" refers to a formulation of a compound that does not cause significant irritation to an organism to which it is administered and does not abrogate the biological activity and properties of the compounds described herein.

As used herein, the term "pharmaceutical combination" means a product that results from the mixing or combining of more than one active ingredient.

As used herein, the term "pharmaceutical composition" refers to a mixture of a compound described herein with other chemical components, such as carriers, stabilizers, diluents, dispersing agents, suspending agents, thickening agents, and/or excipients.

As used herein, the term "prodrug" refers to an agent that is converted into an active or "parent" drug in vivo.

As used herein, the term "solvate" refers to a complex of variable stoichiometry formed by a solute (in this invention, a compound of Formula (I) or a pharmaceutically acceptable salt thereof) and a solvent. Such solvents for the purpose of the invention may not interfere with the biological activity of the solute. Non-limiting examples of suitable solvents include water, acetone, methanol, ethanol and acetic acid. Preferably the solvent used is a pharmaceutically acceptable solvent. Non-limiting examples of suitable pharmaceutically acceptable solvents include water, ethanol and acetic acid.

As used herein, the term "protein kinase-mediated disease" or a "disorder or disease or condition mediated by inappropriate protein kinase activity" refers to any disease state mediated or modulated by protein kinases described herein. Such disease states include, but are not limited to, lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer, and gastrointestinal cancer.

As used herein, the term "Axl-mediated disease" or a "disorder or disease or condition mediated by inappropriate Axl activity" refers to any disease state mediated or modulated by Axl kinase mechanisms. Such disease states include, but are not limited to, AML, ALL, solid tumors, other proliferative disorders, or a condition associated with aberrantly increased levels of Axl kinase.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The term "a subject in need" as used herein refers to any animal, in which a disease associated with the activity of the protein kinase has been or may be developed, such as a monkey, a cow, a horse, a sheep, a pig, a chicken, a turkey, a quail, a cat, a dog, a mouse, a rat, a rabbit and a guinea pig, as well as a human (a patient); and specifically, it may mean a mammal. In addition, the subject in need may be a biological sample.

As used herein, the term "effective amount" or "therapeutically effective amount" refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. By way of example only, a therapeutically effective amount of a compound of Formula (I) may be in the range of e.g., about 0.01 mg/kg/day to about 100 mg/kg/day, or from about 0.1 mg/kg/day to about 10 mg/kg/day.

In one aspect, the present invention provides a use of a compound represented by Formula (I) or a pharmaceutically acceptable salt thereof, as an Axl inhibitor for the treatment of a disease or condition mediated by Axl:

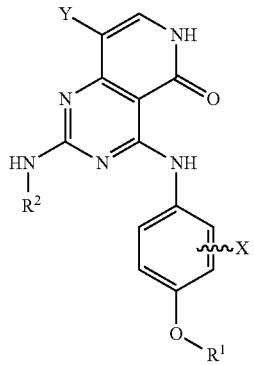

wherein $R^1$ is $C_6$-$C_{10}$aryl, $C_6$-$C_{10}$aryl$C_1$-$C_6$alkyl, $C_5$-$C_6$cycloalkyl or $C_5$-$C_6$cycloalkylmethyl, optionally substituted with one or two $R^3$s;

$R^3$ is independently fluoro, chloro, bromo, iodo, $C_1$-$C_6$alkyl, or trifluoromethyl;

X is H, fluoro, chloro, bromo, iodo, methyl, or trifluoroethyl;

Y is chloro, bromo, iodo, $C_1$-$C_3$alkyl, or phenyl;

$R^2$ is $C_3$-$C_6$cycloalkyl or 4 to 7-membered heterocycloalkyl, wherein the $C_3$-$C_6$cycloalkyl is optionally substituted at carbon atoms with one or two $R^4$s, and wherein the 4 to 7-membered heterocycloalkyl has 1 or 2 heteroatoms selected from the group consisting of nitrogen, oxygen, sulfur, sulfone, or sulfoxide, and is optionally substituted at carbon atom with $R^4$ or at nitrogen atom with $R^5$;

$R^4$ is independently hydroxy, hydroxy$C_1$-$C_6$alkyl, amino, amino$C_1$-$C_6$alkyl, —NH(—$C_1$-$C_3$alkyl), —N(—$C_1$-$C_3$alkyl)$_2$, $C_1$-$C_3$alkyl or halo; and $R^5$ is H, $C_1$-$C_3$alkyl or —C(═O)(—$C_1$-$C_3$alkyl), wherein the $C_1$-$C_3$alkyl is optionally substituted with 1 to 3 fluoros.

In certain embodiments, $R^1$ is phenyl, benzyl, cyclopentyl, cyclohexyl, cyclopentylmethyl, or cyclohexylmethyl, optionally substituted with one or two $R^3$s.

In certain embodiments, $R^3$ is independently fluoro, chloro, methyl, or isopropyl.

In certain embodiments, $R^3$ is independently chloro, fluoro or methyl.

In certain embodiments, $R^3$ is independently chloro or fluoro.

In certain embodiments, X is fluoro or methyl.

In certain embodiments, Y is chloro, bromo, iodo, methyl or phenyl.

In further embodiments, Y is chloro or bromo.

In further embodiments, Y is bromo.

In certain embodiments, $R^2$ is pyrrolidinyl, or piperidinyl.

In certain embodiments, $R^2$ is N-methylpyrrolidinyl or N-methylpiperidinyl.

In certain embodiments, $R^2$ is piperidinyl or pyrrolidinyl substituted at nitrogen atom with $R^5$.

In certain embodiments, $R^5$ is methyl, ethyl, trifluoroethyl, or i-propyl.

In certain embodiments, $R^5$ is methyl.

In certain embodiments, $R^4$ is independently hydroxy, amino, or N-methylamino.

In certain embodiments, the compound of Formula (I) or a pharmaceutically acceptable salt thereof is 8-bromo-2-((1-methylpiperidin-4-yl)amino)-4-((3-phenoxyphenyl)amino)

pyrido[4,3-d]pyrimidin-5(6H)-one hydrochloride, or 8-bromo-4-((4-(3-fluorophenoxy)phenyl)amino)-2-((1-methylpiperidin-4-yl)amino)pyrido[4,3-d]pyrimidin-5(6H)-one hydrochloride.

In certain embodiments, the compound of Formula (I) or a pharmaceutically acceptable salt thereof is 8-bromo-4-((3-fluoro-4-phenoxyphenyl)amino)-2-((1-methylpiperidin-4-yl)amino)pyrido[4,3-d]pyrimidin-5(6H)-one hydrochloride.

In another aspect, the present invention provides a use of individual stereoisomers, mixture of stereoisomers, prodrug derivatives, protected derivatives, N-oxide derivatives, solvates or hydrides of a compound of Formula (I) as defined above, as an Axl inhibitor for the treatment of a disease or condition mediated by Axl. In certain embodiments, the compound of Formula (I) comprises a stereoisomer thereof.

In another aspect, the present invention provides a use of a compound of Formula (I) as defined above or a pharmaceutically acceptable salt thereof, for preparing a medicament for the treatment of a disease or condition mediated by Axl.

Compounds of Formula (I) as defined above or pharmaceutically acceptable salts thereof are useful for treating for the treatment of hyperproliferative diseases associated with, accompanied by and/or caused by Axl hyperfunction, particularly Axl receptor tyrosine kinase induced hyperproliferative diseases.

Compounds of Formula (I) as defined above or pharmaceutically acceptable salts thereof are capable of inhibiting cell proliferation and thus, are suitable for the treatment and/or prevention of Axl receptor tyrosine kinase induced hyperproliferative diseases, particularly selected cancers and primary tumor metastasis.

In certain embodiments, the disease or condition is multiple types of cancer mediated by Axl.

In certain embodiments, the disease or condition is acute lymphoblastic leukemia, acute myeloid leukemia, adrenocortical carcinoma, aids-related cancers, aids-related lymphoma, anal cancer, appendix cancer, astrocytomas, atypical teratoid/rhabdoid tumor, basal cell carcinoma, bile duct cancer, bladder cancer, bone cancer, osteosarcoma and malignant fibrous histiocytoma, brain stem glioma, brain tumor, central nervous system atypical teratoid/rhabdoid tumor, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma, brain and spinal cord tumors, breast cancer, bronchial tumors, burkitt lymphoma, carcinoid tumor, gastrointestinal cancer, central nervous system (CNS) lymphoma, cervical cancer, chordoma, chronic lymphocytic leukemia, chronic myelogenous leukemia, chronic myeloproliferative disorders, colon cancer, colorectal cancer, craniopharyngioma, cutaneous t-cell lymphoma, mycosis fungoides, sezary syndrome, endometrial cancer, ependymoblastoma, ependymoma, esophageal cancer, esthesioneuroblastoma, ewing sarcoma family of tumors, extracranial germ cell tumor, extragonadal germ cell tumor, extrahepatic bile duct cancer, intraocular melanoma, retinoblastoma, gallbladder cancer, gastric (stomach) cancer, gastrointestinal carcinoid tumor, gastrointestinal stromal tumor (gist), gastrointestinal stromal cell tumor, extracranial germ cell tumor, extragonadal germ cell tumor, ovarian germ cell tumor, gestational trophoblastic tumor, glioma, hairy cell leukemia, head and neck cancer, heart cancer, hepatocellular (liver) cancer, histiocytosis, hodgkin lymphoma, hypopharyngeal cancer, intraocular melanoma, islet cell tumors (endocrine pancreas), kaposi sarcoma, renal cell cancer, kidney cancer, langerhans cell histiocytosis, laryngeal cancer, acute lymphoblastic leukemia, acute myeloid leukemia, chronic lymphocytic leukemia, chronic myelogenous leukemia, leukemia, lip and oral cavity cancer, liver cancer, lung cancer, non-small cell lung cancer, small cell lung cancer, aids-related lymphoma, burkitt lymphoma, cutaneous t-cell lymphoma, Hodgkin lymphoma, non-hodgkin lymphoma, primary central nervous system lymphoma, macroglobulinemia, malignant fibrous histiocytoma of bone and osteosarcoma, medulloblastoma, medulloepithelioma, melanoma, intraocular (eye) melanoma, merkel cell carcinoma, mesothelioma, metastatic squamous neck cancer with occult primary, mouth cancer, multiple endocrine neoplasia syndromes, multiple myeloma, plasma cell neoplasm, myelodysplastic syndromes, myelodysplastic/myeloproliferative neoplasms, myelogenous leukemia, myeloid leukemia, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineoblastoma and supratentorial primitive neuroectodermal tumors, pituitary tumor, pleuropulmonary blastoma, pregnancy and breast cancer, prostate cancer, rectal cancer, renal cell (kidney) cancer, transitional cell cancer, respiratory tract cancer, retinoblastoma, rhabdomyosarcoma, salivary gland cancer, sarcoma, ewing sarcoma, kaposi sarcoma, uterine sarcoma, nonmelanoma skin cancer, melanoma skin cancer, skin carcinoma, small cell lung cancer, small intestine cancer, soft tissue sarcoma, squamous cell carcinoma, squamous neck cancer, stomach (gastric) cancer, supratentorial primitive neuroectodermal tumors, t-cell lymphoma, testicular cancer, throat cancer, thymoma and thymic carcinoma, thyroid cancer, transitional cell cancer of the renal pelvis and ureter, trophoblastic tumor, gestational cancer, ureter and renal pelvis cancer, transitional cell cancer, urethral cancer, uterine cancer, endometrial cancer, uterine sarcoma, vaginal cancer, vulvar cancer, Waldenstrom macroglobulinemia, or Wilms tumor.

In another aspect, the present invention provides a pharmaceutical composition comprising a compound of Formula (I) as defined above or a pharmaceutically acceptable salt thereof, in combination with a pharmaceutically acceptable carrier, diluent or excipient.

In another aspect, the present invention provides a pharmaceutical composition comprising a compound of Formula (I) as defined above or a pharmaceutically acceptable salt thereof as an active ingredient, for the treatment of a disease or condition mediated by Axl.

In certain embodiments, the pharmaceutical composition comprises individual stereoisomers, mixture of stereoisomers, prodrug derivatives, protected derivatives, N-oxide derivatives, solvates or hydrides of a compound of Formula (I) as defined above.

Pharmaceutically acceptable salt forms include pharmaceutically acceptable acidic/anionic or basic/cationic salts. Pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate and triethiodide salts. Pharmaceutically acceptable basic/cationic salts include sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid addition salt is formed by reaction of the free base form of a compound of Formula (I) with a suitable inorganic or organic acid including, but not limited to, a hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic (e.g., 2-naphthalenesulfonic) or hexanoic acid.

A pharmaceutically acceptable acid addition salt of a compound of formula (I) can comprise or be, for example, a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

The free acid or free base forms of the compounds of Formula (I) may be prepared from the corresponding base addition salt or acid addition salt from, respectively. For example, a compound of Formula (I) in an acid addition salt form may be converted to the corresponding free base by treating with a suitable base (e.g., ammonium hydroxide solution, sodium hydroxide, and the like). A compound of Formula (I) in a base addition salt form may be converted to the corresponding free acid by treating with a suitable acid (e.g., hydrochloric acid, etc.).

Prodrug derivatives of the compounds of Formula (I) may be prepared by methods known to those of ordinary skill in the art (e.g., for further details see Saulnier et al., (1994), Bioorganic and Medicinal Chemistry Letters, Vol. 4, 1985; the entire teachings of which are incorporated herein by reference).

Protected derivatives of the compounds of Formula (I) may be made by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, the entire teachings of which are incorporated herein by reference.

Compounds of Formula (I) may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of Formula (I), or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981, the entire teachings of which are incorporated herein by reference.

The pharmaceutical composition is formulated as tablets, pills, capsules, a liquid, an inhalant, a nasal spray solution, a suppository, a solution, a gel, an emulsion, an ointment, eye drops or ear drops.

Suitable pharmaceutically acceptable carriers, diluents, adjuvant or excipients for use in the pharmaceutical compositions of the invention include tablets (coated tablets) made of for example collidone or shellac, gum Arabic, talc, titanium dioxide or sugar, capsules (gelatin), solutions (aqueous or aqueous-ethanolic solution), syrups containing the active substances, emulsions or inhalable powders (of various saccharides such as lactose or glucose, salts and mixture of these excipients with one another) and aerosols (propellant-containing or free inhale solutions).

Excipients which may be used include, for example, water, pharmaceutically acceptable organic solvents such as paraffins (e.g., petroleum fractions), vegetable oils (e.g. groundnut or sesame oil), mono- or polyfunctional alcohols (e.g., ethanol or glycerol), carriers such as natural mineral powders (e.g., kaoline, clays, talc, chalk), synthetic mineral powders (e.g., highly dispersed silicic acid and silicates), sugars (e.g., cane sugar, lactose and glucose), emulsifiers (e.g., lignin, spent sulphite liquors, methylcellulose, starch and polyvinylpyrrolidone) and lubricants (e.g., magnesium stearate, talc, stearic acid and sodium lauryl sulphate).

In another aspect, the present invention provides a method for treating a disease or condition mediated by Axl, comprising administering to a subject in need thereof an effective amount of a compound of Formula (I) as defined above or a pharmaceutically acceptable salt thereof.

In another aspect, the present invention provides a method for inhibiting Axl receptor tyrosine kinase or for inhibiting growth of cancer cells.

In addition, the compound is administered singly or in combination with one or more additional therapeutic agents such as immunotherapy (anti-PD-1 and/or anti-CTLA4), chemotherapy and irradiation.

In certain embodiments, the compound is administered singly or in combination with one or more immune checkpoint blockers (anti-PD-1, anti-PDL, anti-CLTA4), and additional chemotherapeutic agents The methods of administration of such compounds and compositions include, but are not limited to, intravenous administration, inhalation, oral administration, rectal administration, parenteral, intravitreal administration, subcutaneous administration, intramuscular administration, intranasal administration, dermal administration, topical administration, ophthalmic administration, buccal administration, tracheal administration, bronchial administration, sublingual administration or otic administration. Compounds provided herein are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

In certain embodiments, the compound is administered via intravenous administration, subcutaneous administration, inhalation, oral administration, rectal administration, parenteral, intravitreal administration, intramuscular administration, intranasal administration, dermal administration, topical administration, optic administration, ophthalmic administration, buccal administration, tracheal administration, bronchial administration, or sublingual administration.

In the above methods, a compound of Formula (I) as defined above or a pharmaceutically acceptable salt thereof is administered to a system comprising cells or tissues. In certain embodiments, a compound of Formula (I) as defined above or a pharmaceutically acceptable salt thereof is administered to a human or animal subject.

The therapeutically effective amount will vary depending on, among others, the disease indicated, the severity of the disease, the age and relative health of the subject, the potency of the compound administered, the mode of administration and the treatment desired.

The required dosage will also vary depending on the mode of administration, the particular condition to be treated and the effect desired.

The compound of Formula (I) as defined above is prepared by:
  (a) optionally converting a compound of Formula (I) into a pharmaceutically acceptable salt;
  (b) optionally converting a salt form of a compound of Formula (I) to a non-salt form;
  (c) optionally converting an unoxidized form of a compound of Formula (I) into a pharmaceutically acceptable N-oxide;
  (d) optionally resolving an individual isomer of a compound of Formula (I) from a mixture of isomers;
  (e) optionally converting a non-derivatized compound of Formula (I) into a pharmaceutically acceptable prodrug derivative; and
  (f) optionally converting a prodrug derivative of a compound of Formula (I) to its non-derivatized form.

Modes for the Invention

Hereinafter, the present invention will be described in detail with reference to examples. However, the following examples are for illustrative purposes only and are not intended to limit the scope of the invention. Those skilled in the art will appreciate that variations and modifications can be made without changing the scope of the invention.

Liquid Chromatography-Mass Spectrometry (LC-MS) Method:
  1. Samples are run on Agilent Technologies 6120 MSD system with a Zorbax Eclipse XDB-C18 (3.5 μm) reverse phase column (4.6×50 mm) run at room temperature with flow rate of 1.5 mL/minute.
  2. The mobile phase uses solvent A (water/0.1% formic acid) and solvent B (acetonitrile/0.1% formic acid): 95%/5% to 0%/100% (A/B) for 5 minute.
  3. The mass spectra (m/z) were recorded using electrospray ionization (ESI).
  4. Ionization data was rounded to the nearest integer.

The preparation of compounds of Formula (I) or pharmaceutically acceptable salts thereof as defined above is described in Example and Table 1 of PCT Publication No. WO 2013/142382, which was filed on 15 Mar. 2013, and in equivalent applications and patents in numerous other countries, e.g. in U.S. Pat. No. 8,877,763, Australian Patent No. 2013235344, Japanese Patent No. 6101341, and Chinese Patent No. 104428298. The teachings of all patents, published applications and references cited herein are incorporated by reference in their entirety.

Certain compounds of Formula (I) or pharmaceutically acceptable salts thereof are named as follows:

221. 4-((4-(benzyloxy)phenyl)amino)-8-bromo-2-((1-methylpiperidin-4-yl)amino)pyrido[4,3-d]pyrimidin-5(6H)-one;
222. 8-bromo-2-((1-methylpiperidin-4-yl)amino)-4-((4-phenoxyphenyl)amino)pyrido[4,3-d]pyrimidin-5(6H)-one;
223. 8-bromo-4-((4-(cyclopentyloxy)phenyl)amino)-2-((1-methylpiperidin-4-yl)amino)pyrido[4,3-d]pyrimidin-5(6H)-one;
224. 8-bromo-4-((4-(cyclohexylmethoxy)phenyl)amino)-2-((1-methylpiperidin-4-yl)amino)pyrido[4,3-d]pyrimidin-5(6H)-one;
225. 8-bromo-2-((1-methylpiperidin-4-yl)amino)-4-((4-(p-tolyloxy)phenyl)amino)pyrido[4,3-d]pyrimidin-5(6H)-one;
226. 8-bromo-2-((1-methylpiperidin-4-yl)amino)-4-((4-phenoxyphenyl)amino)pyrido[4,3-d]pyrimidin-5(6H)-one hydrochloride;
227. 8-bromo-4-((4-(cyclopentylmethoxy)phenyl)amino)-2-((1-methylpiperidin-4-yl)amino)pyrido[4,3-d]pyrimidin-5(6H)-one;
228. 8-bromo-4-((4-(cyclohexyloxy)phenyl)amino)-2-((1-methylpiperidin-4-yl)amino)pyrido[4,3-d]pyrimidin-5(6H)-one;
229. 8-chloro-4-((4-(cyclohexyloxy)phenyl)amino)-2-((1-methylpiperidin-4-yl)amino)pyrido[4,3-d]pyrimidin-5(6H)-one;
230. 8-bromo-4-((4-(4-isopropylphenoxy)phenyl)amino)-2-((1-methylpiperidin-4-yl)amino)pyrido[4,3-d]pyrimidin-5(6H)-one;
231. 8-bromo-2-((1-methylpiperidin-4-yl)amino)-4-((4-(p-tolyloxy)phenyl)amino)pyrido[4,3-d]pyrimidin-5(6H)-one hydrochloride;
232. 8-bromo-4-((4-(4-fluorophenoxy)phenyl)amino)-2-((1-methylpiperidin-4-yl)amino)pyrido[4,3-d]pyrimidin-5(6H)-one hydrochloride;
233. 8-bromo-4-((4-(cyclohexyloxy)phenyl)amino)-2-((1-methylpiperidin-4-yl)amino)pyrido[4,3-d]pyrimidin-5(6H)-one hydrochloride;
234. 4-((4-(benzyloxy)phenyl)amino)-8-bromo-2-((1-methylpiperidin-4-yl)amino)pyrido[4,3-d]pyrimidin-5(6H)-one hydrochloride;
235. 8-bromo-4-((4-(cyclopentylmethoxy)phenyl)amino)-2-((1-methylpiperidin-4-yl)amino)pyrido[4,3-d]pyrimidin-5(6H)-one hydrochloride;
236. 8-bromo-4-((4-(4-isopropylphenoxy)phenyl)amino)-2-((1-methylpiperidin-4-yl)amino)pyrido[4,3-d]pyrimidin-5(6H)-one hydrochloride;
237. 8-bromo-4-((4-(cyclopentyloxy)phenyl)amino)-2-((1-methylpiperidin-4-yl)amino)pyrido[4,3-d]pyrimidin-5(6H)-one hydrochloride;
238. 8-bromo-4-((4-(3-fluorophenoxy)phenyl)amino)-2-((1-methylpiperidin-4-yl)amino)pyrido[4,3-d]pyrimidin-5(6H)-one hydrochloride;
239. 8-bromo-2-((1-methylpiperidin-4-yl)amino)-4-((4-(o-tolyloxy)phenyl)amino)pyrido[4,3-d]pyrimidin-5(6H)-one hydrochloride;
240. 8-bromo-4-((4-(3-fluorophenoxy)phenyl)amino)-2-((1-methylpiperidin-4-yl)amino)pyrido[4,3-d]pyrimidin-5(6H)-one;
241. 8-bromo-4-((4-(3,4-difluorophenoxy)phenyl)amino)-2-((1-methylpiperidin-4-yl)amino)pyrido[4,3-d]pyrimidin-5(6H)-one hydrochloride;
242. 8-bromo-4-((4-(4-chlorophenoxy)phenyl)amino)-2-((1-methylpiperidin-4-yl)amino)pyrido[4,3-d]pyrimidin-5(6H)-one hydrochloride;

243. 8-bromo-4-((4-(3,5-difluorophenoxy)phenyl)amino)-2-((1-methylpiperidin-4-yl)amino)pyrido[4,3-d]pyrimidin-5(6H)-one hydrochloride;

244. 8-bromo-4-((4-(3-fluorophenoxy)-3-methylphenyl)amino)-2-((1-methylpiperidin-4-yl)amino)pyrido[4,3-d]pyrimidin-5(6H)-one hydrochloride;

245. 8-bromo-4-((3-fluoro-4-phenoxyphenyl)amino)-2-((1-methylpiperidin-4-yl)amino)pyrido[4,3-d]pyrimidin-5(6H)-one hydrochloride;

246. 8-bromo-4-((3-methyl-4-phenoxyphenyl)amino)-2-((1-methylpiperidin-4-yl)amino)pyrido[4,3-d]pyrimidin-5(6H)-one hydrochloride;

247. 8-bromo-4-((3-fluoro-4-(3-fluorophenoxy)phenyl)amino)-2-((1-methylpiperidin-4-yl)amino)pyrido[4,3-d]pyrimidin-5(6H)-one hydrochloride;

248. 8-bromo-2-(1-isopropylpiperidin-4-ylamino)-4-(4-phenoxyphenylamino)pyrido[4,3-d]pyrimidin-5(6H)-one;

249. 8-bromo-2-(1-ethylpiperidin-4-ylamino)-4-(4-phenoxyphenylamino)pyrido[4,3-d]pyrimidin-5(6H)-one; and 250. 8-bromo-4-(4-phenoxyphenylamino)-2-(1-(2,2,2-trifluoroethyl)piperidin-4-ylamino)pyrido[4,3-d]pyrimidin-5(6H)-one.

Table 1 shows the structures of compounds of Formula (I).

All data are listed in a range of $IC_{50}$ value (Axl).

Each ++++, +++, ++ and + indicated 1-10 nM, 11-100 nM, 101-1000 nM, 1001-10000 nM, respectively.

TABLE 1

| No | Structure | MS (ESI+) m/z | Axl ($IC_{50}$) |
|---|---|---|---|
| 221 | | 535 | ++ |
| 222 | 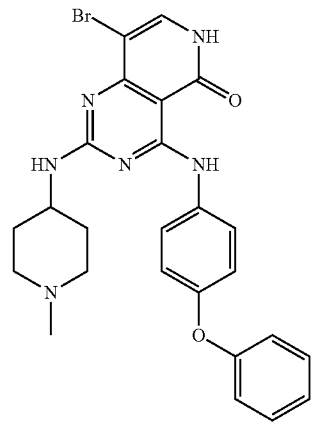 [SMILES: CN1CCC(Nc2nc(Nc3ccc(Oc4ccccc4)cc3)c3c(=O)[nH]cc(Br)c3n2)CC1] | 521 | +++ |
| 223 | 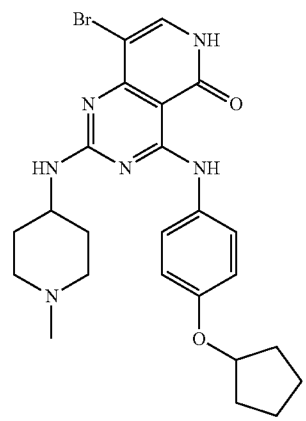 [SMILES: CN1CCC(Nc2nc(Nc3ccc(OC4CCCC4)cc3)c3c(=O)[nH]cc(Br)c3n2)CC1] | 513 | ++ |
| 224 | 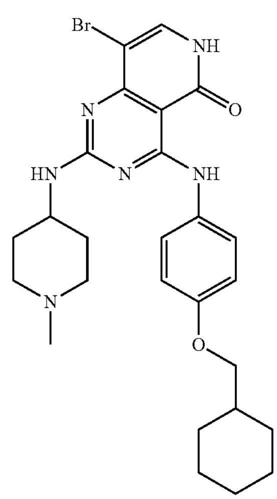 [SMILES: CN1CCC(Nc2nc(Nc3ccc(OCC4CCCCC4)cc3)c3c(=O)[nH]cc(Br)c3n2)CC1] | 541 | ++ |

TABLE 1-continued

| No | Structure | MS (ESI+) m/z | Axl (IC$_{50}$) |
|---|---|---|---|
| 225 | 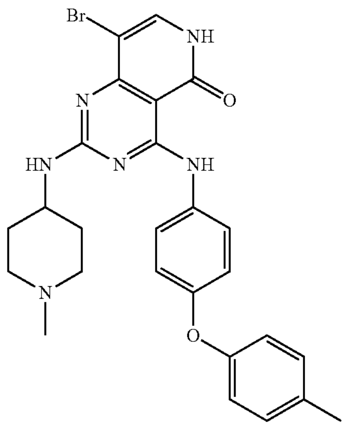 [SMILES: Cc1ccc(Oc2ccc(Nc3nc(NC4CCN(C)CC4)nc4c(Br)c[nH]c(=O)c34)cc2)cc1] | 535 | +++ |
| 226 | 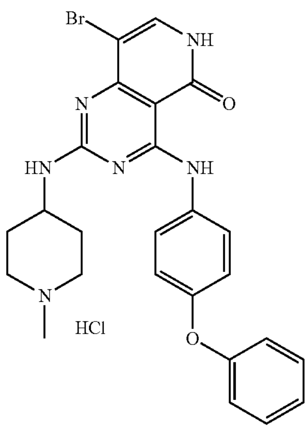 [SMILES: CN1CCC(Nc2nc(Nc3ccc(Oc4ccccc4)cc3)c3c(=O)[nH]cc(Br)c3n2)CC1 ; Cl] | 521 | +++ |
| 227 | 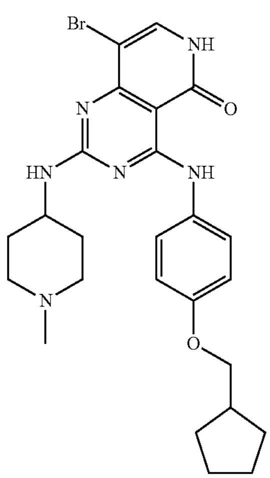 [SMILES: CN1CCC(Nc2nc(Nc3ccc(OCC4CCCC4)cc3)c3c(=O)[nH]cc(Br)c3n2)CC1] | 527 | ++ |
| 228 | 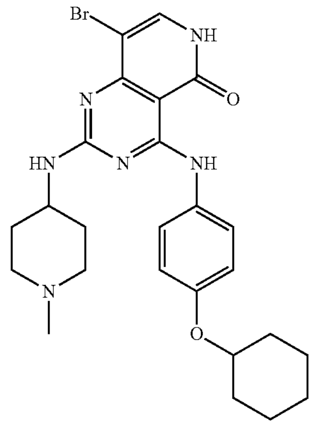 [SMILES: CN1CCC(Nc2nc(Nc3ccc(OC4CCCCC4)cc3)c3c(=O)[nH]cc(Br)c3n2)CC1] | 527 | ++ |
| 229 | 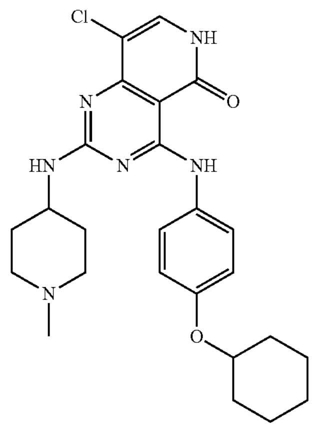 [SMILES: CN1CCC(Nc2nc(Nc3ccc(OC4CCCCC4)cc3)c3c(=O)[nH]cc(Cl)c3n2)CC1] | 483 | ++ |
| 230 | 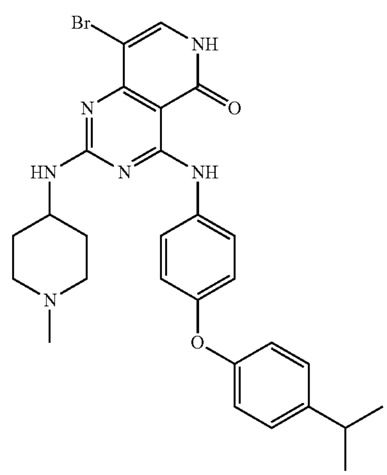 [SMILES: CC(C)c1ccc(Oc2ccc(Nc3nc(NC4CCN(C)CC4)nc4c(Br)c[nH]c(=O)c34)cc2)cc1] | 563 | +++ |

TABLE 1-continued

| No | Structure | MS (ESI+) m/z | Axl (IC$_{50}$) |
|----|-----------|---------------|-----------------|
| 231 | 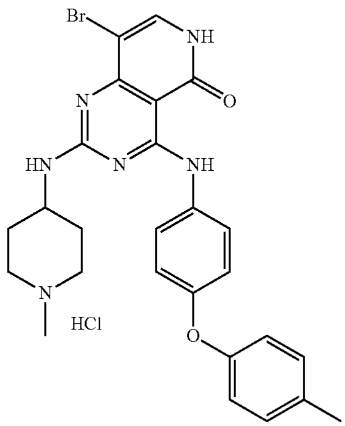 [SMILES: Cc1ccc(Oc2ccc(Nc3nc(NC4CCN(C)CC4)nc4c(Br)c[nH]c(=O)c34)cc2)cc1 ; Cl] | 535 | +++ |
| 232 | 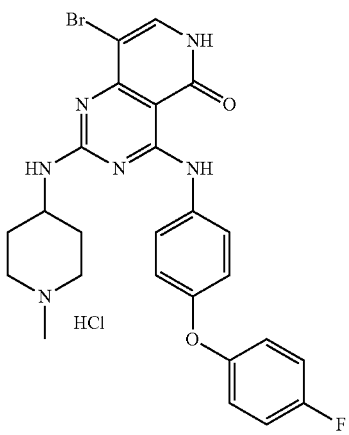 [SMILES: CN1CCC(Nc2nc(Nc3ccc(Oc4ccc(F)cc4)cc3)c3c(=O)[nH]cc(Br)c3n2)CC1 ; Cl] | 539 | +++ |
| 233 | 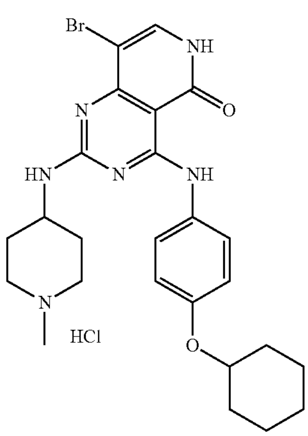 [SMILES: CN1CCC(Nc2nc(Nc3ccc(OC4CCCCC4)cc3)c3c(=O)[nH]cc(Br)c3n2)CC1 ; Cl] | 527 | ++ |
| 234 | | 535 | ++ |
| 235 | | 527 | ++ |
| 236 | | 563 | +++ |

TABLE 1-continued
| No | Structure | MS (ESI+) m/z | Axl (IC$_{50}$) |
|---|---|---|---|
| 237 | 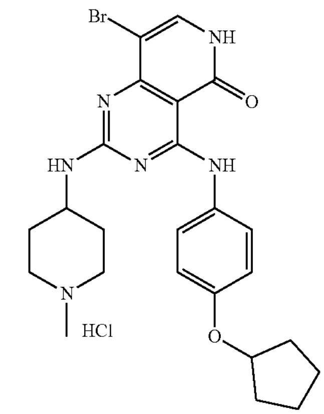 [SMILES: CN1CCC(Nc2nc(Nc3ccc(OC4CCCC4)cc3)c3c(=O)[nH]cc(Br)c3n2)CC1 ; Cl] | 513 | ++ |
| 238 | 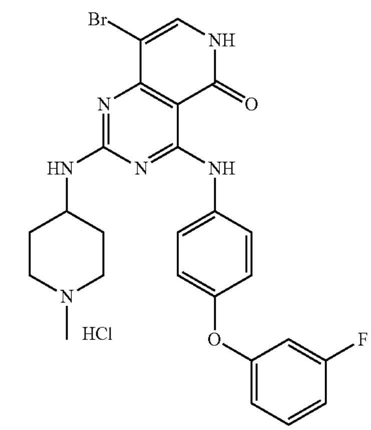 [SMILES: CN1CCC(Nc2nc(Nc3ccc(Oc4cccc(F)c4)cc3)c3c(=O)[nH]cc(Br)c3n2)CC1 ; Cl] | 539 | +++ |
| 239 | 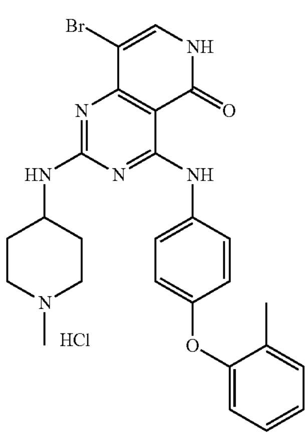 | 535 | +++ |
| 240 | | 539 | +++ |
| 241 | | 557 | +++ |
| 242 | | 555 | +++ |
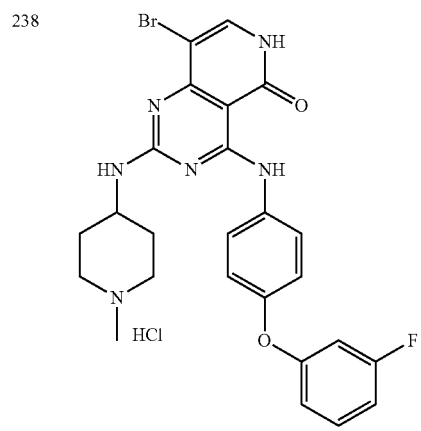
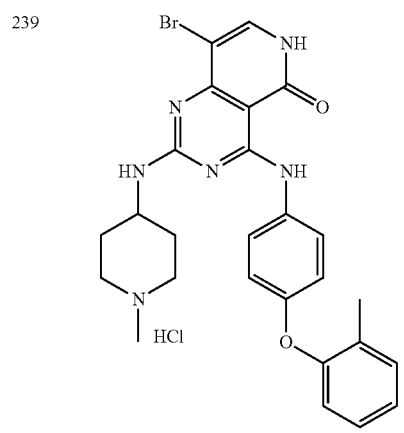

TABLE 1-continued

| No | Structure | MS (ESI+) m/z | Axl (IC50) |
|---|---|---|---|
| 243 | 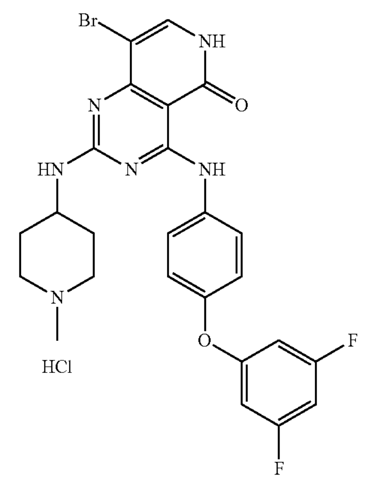 [SMILES: CN1CCC(Nc2nc(Nc3ccc(Oc4cc(F)cc(F)c4)cc3)c3c(=O)[nH]cc(Br)c3n2)CC1 ; Cl] | 557 | +++ |
| 244 | 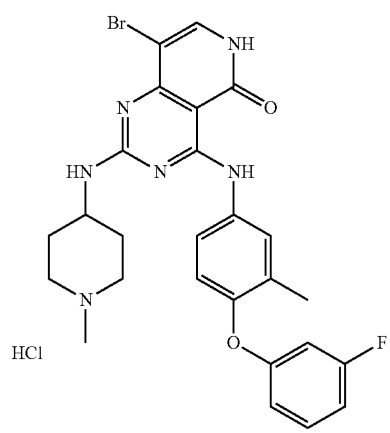 [SMILES: Cl ; Cc1cc(Nc2nc(NC3CCN(C)CC3)nc3c(Br)c[nH]c(=O)c23)ccc1Oc1cccc(F)c1] | 553 | +++ |
| 245 | 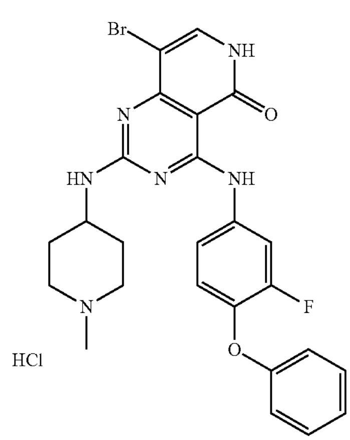 [SMILES: Cl ; Cc1cc(Nc2nc(NC3CCN(C)CC3)nc3c(Br)c[nH]c(=O)c23)ccc1Oc1ccccc1] | 539 | +++ |
| 246 | | 535 | +++ |
| 247 | | 557 | +++ |
| 248 | | 549 | +++ |

TABLE 1-continued

| No | Structure | MS (ESI+) m/z | Axl (IC$_{50}$) |
|----|-----------|---------------|-----------------|
| 249 | (structure: 8-bromo pyrido[4,3-d]pyrimidin-5(6H)-one with (1-ethylpiperidin-4-yl)amino and (4-phenoxyphenyl)amino substituents) | 535 | +++ |
| 250 | (structure: 8-bromo pyrido[4,3-d]pyrimidin-5(6H)-one with (1-(2,2,2-trifluoroethyl)piperidin-4-yl)amino and (4-phenoxyphenyl)amino substituents) | 589 | ++ |

The contents of all patents, patent applications, and publications listed herein are incorporated herein by reference.

BIOLOGICAL ASSAYS

1. Kinase Inhibition Assay (Inhibition of Enzymatic Axl Kinase Activity)

Compounds of Formula (I) as obtained above were assayed to measure their capacity to inhibit Axl kinase. Axl belongs to the recently identified TYRO-3, Axl, MERTK (TAM) receptor tyrosine kinase (RTK) family. The growth arrest-specific 6 (GAS6) protein serves as a common ligand for each TAM kinase and shows highest affinity for Axl. Upon GAS6 binding, Axl homodimerizes and subsequently induces several downstream signaling pathways involved in cell proliferation, migration, invasion, anti-apoptosis, angiogenesis, metastasis, and therapeutic resistance. Upregulation of Axl has been reported in a wide variety of cancer cell lines as well as in cancer specimens from patients with breast cancer, acute leukemia, colorectal cancer, lung cancer, melanoma, ovarian cancer, or prostate cancer, among others.

Methods

Compounds of Formula (I) as obtained above were initially diluted to 10 nM in 100% DMSO (CALBIOCHEM™) for storage and made into kinase buffer solution to create a compound concentration ranging from 1 uM and 10 uM. Serial dilutions of the compounds were dispensed into a 96-well plate (GREINER BIOSCIENCES™) at 6 μL each. Truncated human Axl (CARNA BIOSCIENCES™) were diluted in kinase buffer and added to the compound solutions and pre-incubated for 30 minutes at room temperature. Next, ATP (TEKNOVA™) and substrate solution (suggested manufacture substrates of PERKINELMER™, for example, ULIGHT™-TK peptide) for Axl (PERKINELMER™) was added (12 μL each) to the wells containing the compound solution and enzyme. The reaction mixture was incubated for 1 hour. Following the incubation, the stop solution made with EDTA, water, and Lance detection buffer (PERKINELMER™) were added (12 μL each) to stop phosphorylation. Following the addition of the stop solution and 5 minutes of shaking, the detection solution containing the Europium-labeled antibody (suggested manufacture substrates of PERKINELMER™, for example, PT66 for Axl), water, and Lance detection buffer were added (12 μL) to the reaction mixture and incubated again for 50 minutes. Substrate phosphorylation was a function of the 665 nm emission measured following the addition of the detection solution and 50 minutes of incubation.

Results

Compounds of Formula (I) exhibited useful pharmacological properties. As used herein, an way to describe potency of inhibitory activity (nM) is a range of inhibitory activity at 50% (IC$_{50}$) as shown in Table 2. Reference compounds, ASP2215 (gilteritinib, Astellas), R428 (BGB324, BerGenBio) and staurosporine (pan-kinase inhibitor) were used for Axl to judge inhibitory activity of compounds of Formula (I).

For example, the compound 238 of Formula (I), namely, 8-bromo-4-((4-(3-fluorophenoxy)phenyl)amino)-2-((1-methylpiperidin-4-yl)amino)pyrido[4,3-d]pyrimidin-5(6H)-one hydrochloride, showed strong inhibition of kinase activity of Axl. Its potency in biochemical assay is comparable to that of clinically developing Axl inhibitors, APS2215 and R428. Table 2 illustrates a range of IC$_{50}$ value of Axl by the representative compounds of Formula (I). As shown in Table 2, the reference compound, staurosporine, is the most potent, whereas compounds of Formula (I) as obtained above show better selectivity than the reference compound and display similar potency to ASP2215 and R428. Furthermore, the compounds of Formula (I) also show better selectivity than those indicated by asterisk and described in WO 2011/053861 and PCT/US2010/054853. Taken together, these data suggest that the compounds of Formula (I) significantly improve selectivity as well as inhibitory potency in Axl compared to known the Axl inhibitors, ASP2215 and R428.

The compounds No. 8 and 136 described in WO 2011/053861 showed multiple inhibitory activities against various tested kinases including JAK2. In particular, they showed no drug exposure in rat after oral administration of 10 mg/kg, suggesting that they were not absorbed in gut or were eliminated extremely fast from body.

Table 2 shows the biochemical inhibition of Axl and JAK2 by the representative compounds of Formula (I).

TABLE 2

| Compound | Axl | JAK2 | Compound | Axl | JAK2 |
|----------|-----|------|----------|-----|------|
| ASP2215 | +++ | +++ | 223 | ++ | ++ |
| R428 | +++ | ++ | 225 | +++ | + |
| *8 | +++ | +++ | 226 | +++ | ++ |

TABLE 2-continued

| Compound | Axl | JAK2 | Compound | Axl | JAK2 |
|---|---|---|---|---|---|
| *136 | +++ | ++++ | 228 | ++ | ++ |
| *203 | +++ | ++ | 233 | ++ | ++ |
| 222 | +++ | ++ | 240 | +++ | ++ |
| 241 | +++ | + | 238 | +++ | ++ |
|  |  |  | Staurosporine | ++++ | ++++ |

*Compounds 8, 136 and 203 were described in WO 2011/053861 and PCT/US2010/054853.
All data are listed in a range of $IC_{50}$ value. Each ++++, +++, ++ and + indicated 1-10 nM, 11-100 nM, 101-1000 nM, 1001-10000 nM, respectively.

2. Cell Viability Assay: Inhibition of Proliferation of Axl-Positive Cells

Compounds of Formula (I) as obtained above are tested for their effects on inhibition of proliferation of Axl-harboring triple-negative breast cancer cell lines (MDA-MB-231 and Hs578T) and Axl negative breast cancer cell lines (MCF7). Axl is a member of the TAM (TYRO3-Axl-MER) family of receptor tyrosine kinases, which, when activated, can increase tumor cell survival, proliferation, migration and invasion, angiogenesis, and tumor-host interactions. Upon GAS6 binding to Axl, Axl subsequently activates the signaling pathways downstream such as phosphoinositide 3-kinase (PI3K), RAt sarcoma (RAS), and extracellular signal regulated kinase (ERK).

Overexpression or aberrant activation of Axl has been described in multiple malignancies from epithelial and hematological origins and is often associated with poor prognosis, increased relapse rate, decreased disease-free survival, and poor overall survival. Moreover, Axl expression is associated with epithelial to mesenchymal transition (EMT), a frequent feature of metastatic tumors often correlated to drug resistance. Therefore, Axl is an attractive molecular target for multiple solid tumors including breast cancer.

Methods

Compounds of Formula (I) as obtained above were tested for cell viability effect on MDA-MB-231 and Hs578T cells. For cell viability assay, MDA-MB-231 and Hs578T cells expressing human Axl were obtained from the American Type Culture Collection (ATCC, Manassas, VA). This cell line was maintained with an Roswell Park Memorial Institute (RPMI) medium (HYCLONE™) containing 10% bovine calf serum (BCS; HYCLONE™) supplemented iron. The cells were seeded at $2 \times 10^4$ cells in 96-well culture plates, and serially diluted compounds were then added. After a 72 hour incubation period at 37° C., cell viability was measured using the ATPLite 1 step assay (PERKIN-ELMER™) that is based on the quantification of ATP from viable cells. The concentrations for 50% of maximal inhibition of cell proliferation ($GI_{50}$ values) were calculated using nonlinear regression and defined as the concentration needed for a 50% reduction in luminescence or absorbance of treated versus untreated control cells (Prism™ Software).

Results

The $GI_{50}$ inhibition data of the representative compounds of Formula (I) are shown in Table 3. Compounds of Formula (I) exhibited an inhibition of cell proliferation with less than 3 μM $GI_{50}$ value. Specially, the compound 237, 8-bromo-4-((4-(cyclopentyloxy)phenyl)amino)-2-((1-methylpiperidin-4-yl)amino)pyrido[4,3-d]pyrimidin-5(6H)-one hydrochloride, exhibited an inhibition level greater than those exhibited by reference ASP2215 and R428 in Axl-harboring breast cancer cell lines. Such strong anti-tumor activity suggests that the compounds of Formula (I) are better therapeutic value than the reference and the compound 203 indicated by asterisks described in PCT Application No. PCT/US2010/054853.

Table 3 shows a cell viability by Axl positive cancer cell line by the representative compounds of Formula (I).

TABLE 3

| Compound | MDA-MB-231 ($GI_{50}$) | Hs578T ($GI_{50}$) | Compound | MDA-MB-231 ($GI_{50}$) | Hs578T ($GI_{50}$) |
|---|---|---|---|---|---|
| ASP2215 | ++ | ++ | 222 | ++ | ++ |
| R428 | + | ++ | 226 | ++ | ++ |
| *203 | +++ | +++ | 228 | ++ | ++ |
| 228 | +++ | +++ | 235 | +++ | +++ |
| 233 | ++ | +++ | 238 | +++ | +++ |
| 237 | +++ | ++++ | 241 | ++ | ++ |
|  |  |  | 240 | ++ | ++ |

*Compound 203 was described in WO 2011/053861 and PCT/US2010/054853.
All data are listed in a range of $GI_{50}$ value. Each ++++, +++, ++ and + indicated 0.1-1.0 μM, 1.1-3.0 μM, 3.1-10 μM, 11-30 μM, respectively.

3. Migration and Invasion Assay: Inhibition of Metastatic Potential

In order to test whether the compounds of Formula (I) show the effect on inhibition of metastasis, cell migratory and invasive behaviors analyzed using transwell and matrigel invasion assays in MDA-MB-231 breast cancer cell line.

Methods

Figure 1B:
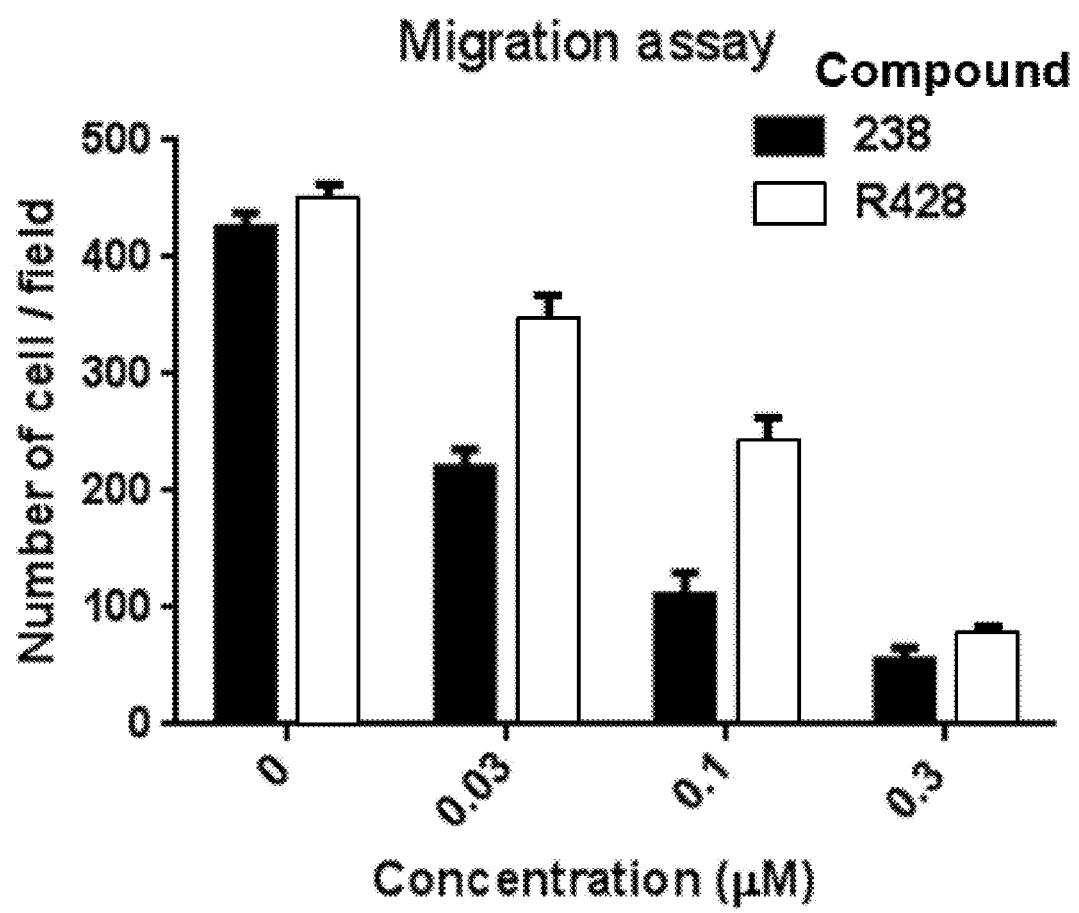
Figure 1C:
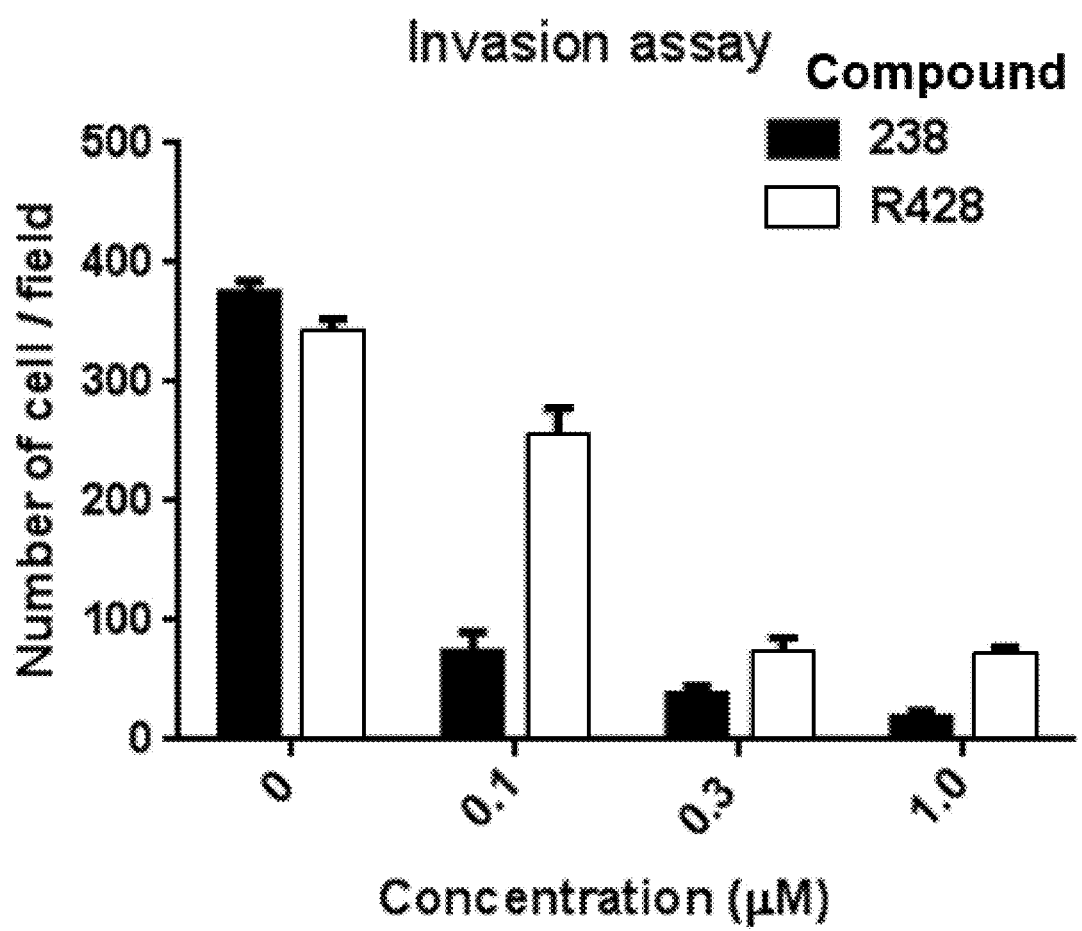

Compounds of Formula (I) as obtained above were tested in migration and invasion assays using MDA-MB-231 breast cancer cell line. Cell migration was performed by the transwell assay (BD Biosciences, CA, USA). Briefly, $5 \times 10^4$ cells in serum-free RPMI-1640 were seeded on a membrane (8.0-μm pore size) inserted in the wells of a 24-well plate. RPMI-1640 containing 10% FBS was added to the lower chamber of each well. After 24 h, cells in the upper chamber were removed by cotton swab and the cells that had reached the underside of the membrane were fixed and stained with crystal violet (1% in methyl alcohol) for 10 min. The cells located on the underside of the filter (5 fields/filter) were counted. The cell invasion assay was carried out similarly, except that the matrigel (BD Biosciences, CA, USA) was added to each well 6 h before cells were seeded on the membrane. After 48 h, matrigel and any remaining cells in the upper chamber were removed by cotton swabs. Cells on the lower surface of the membrane were fixed and stained as described above. The compound 238 and the reference compound, R428, were incubated as indicated in FIGS. 1a to 1c. Data are representative of results from three independent fields of stained membrane.

Results

As shown in FIGS. 1a to 1c, the representative compound 238 of Formula (I) shows impaired migratory and invasive abilities of MDA-MB-231 cells, which is superior to the reference compound, R428. Interestingly, the representative compound 238 of Formula (I) significantly inhibited the migration and invasion even at 0.03 μM, compared to R428. These results suggest that the representative compound is very potent anti-metastatic activity using MDA-MB-231 cells. Furthermore, the compound of Formula (I) as obtained above would confer a therapeutic option for metastasis associated with Axl expression such as aggressive in breast cancer.

4. Anti-Tumor Activity in Breast 4T1 Syngeneic In Vivo Cancer Models

In order to test whether the compounds of Formula (I) show anti-tumor activity in breast 4T1 syngeneic in vivo cancer models, they were tested as follows.

Methods

Compounds of Formula (I) as obtained above were tested in syngeneic model using mouse breast 4T1 cancer cells. 4T1 cells were grown in RPMI1640 medium (Sigma, Cat #R6504) supplemented with 10% FBS (Invitrogen, Cat #10438-026), and 1% penicillin streptomycin (Thermo Fisher Scientific, Cat #15140-122). The cells were harvested by trypsinization when they reached 70-80% confluence. A day before cell inoculation, fur on the right flank of BALB/C mice was depilated using hair trimmer. On the following day, the skin area around the injection site was disinfected by mildly swabbing with surgical spirit. To establish allografts, cells were suspended in serum-free media and mixed 1:1 with matrigel to obtain $1\times10^6$ cells/100 μL. Cells suspended in matrigel were implanted subcutaneously using a 1 mL BD syringe attached to a 24 gauge needle (BD Precision Glide needles, 0.55 mm×25 mm, REF #302805). Mice were randomized based on tumor volume and six mice were allocated per group. Tumor grafts were measured after approximately 5 days of cell inoculation when they become palpable. Animals were orally administered with vehicle control or the compound 238 (QD, 30 mg/kg/day) once a day for 14 days. Vehicle for oral administration consists of 10% sodium sulphobutylether β-cyclodextrine (SBECD) in 50 mM citrate buffer (pH 3.0). Tumor growth inhibition (TGI) was calculated as follows: % TGI=[1−(Treatment $TV_{Final}$−Treatment $TV_{initial}$)/(Control $TV_{Final}$−Control $TV_{Initial}$)]*100

Results

Figure 2A:
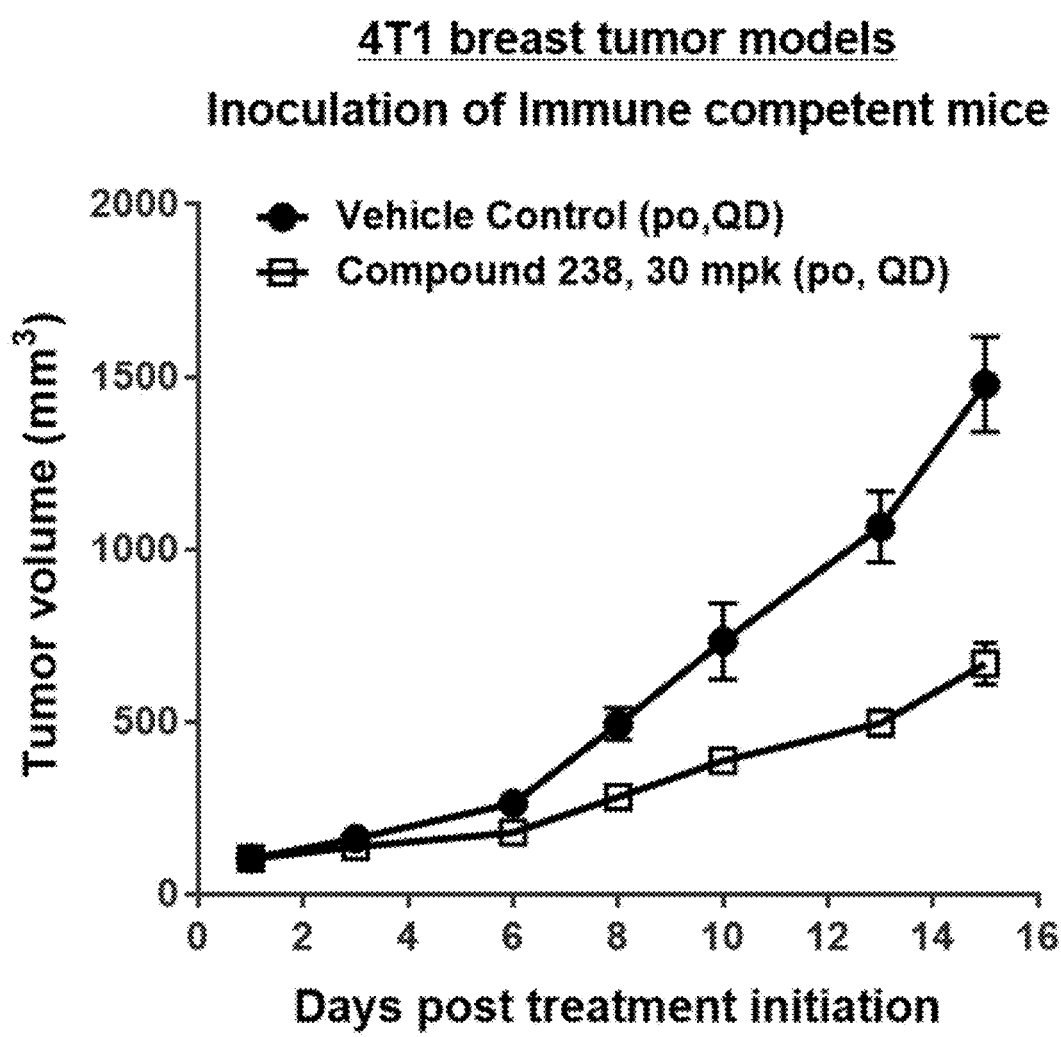
FIGS. 2a and 2b show an anti-tumor activity of compound 238 in breast 4T1 syngeneic in vivo cancer models.

The objective of this study was to test anti-tumor efficacy of the compound 238 stand alone in breast 4T1 syngenic tumor model. All treatments were well tolerated as there were no clinical signs of abnormality and significant changes in animal body weight compared to vehicle control. On day 15, the average tumor volume of treatment group #2 (compound 238) was 669±60 mm³ that resulted in tumor growth inhibition (TGI) of 59% (see FIG. 2a). Overall, these results suggest that the compound 238 shows good anti-tumor activity in the immunocompetant 4T1 syngeneic tumor model in BALB/C mice.

Figure 2B:
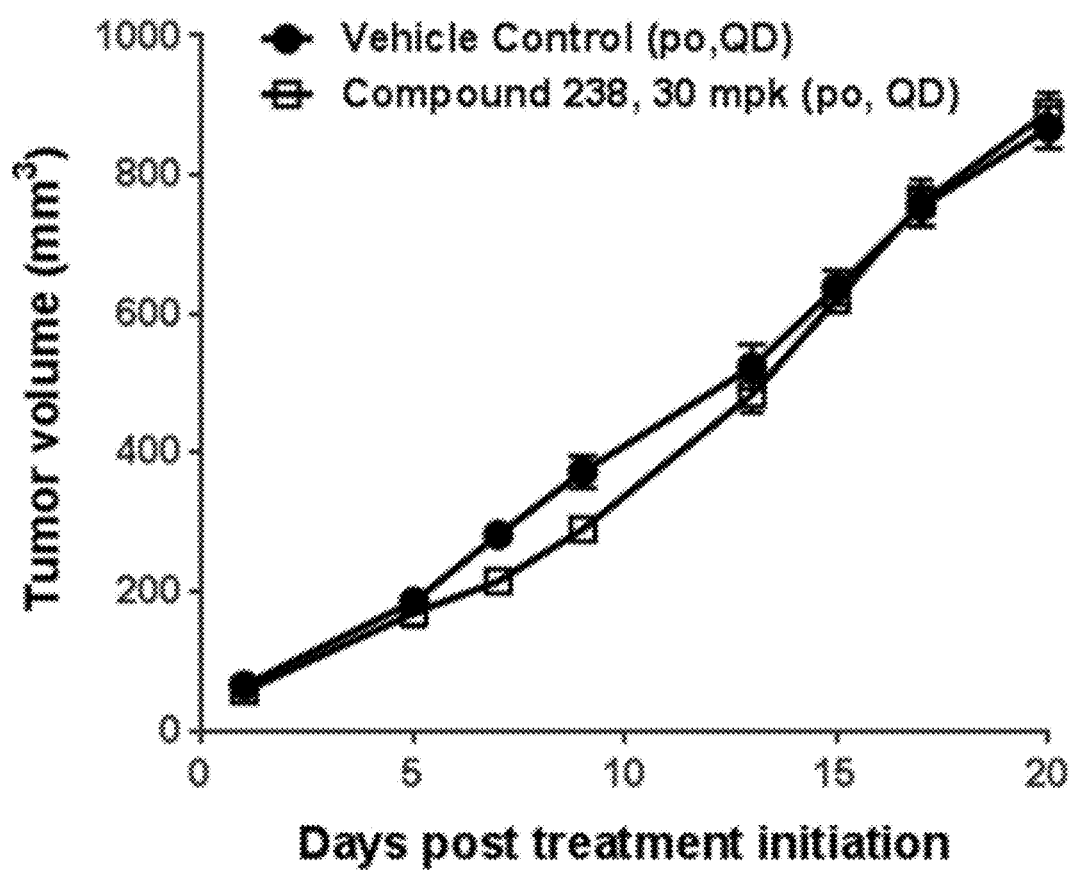

Interestingly, there is no anti-tumor effect of 30 mg/kg/day of compound 238 in immunodeficient mice (see FIG. 2b), indicating that it can suppress tumor growth by directly increasing immune response.

5. Anti-Metastatic Activity in Breast 4T1 Syngeneic In Vivo Cancer Models

In order to test whether the compounds of Formula (I) show anti-cancer metastatic activity in B16F10 lung and CT-26 peritoneal metastasis models, they were tested as follows.

Methods

Compounds of Formula (I) as obtained above were tested in metastasis models using mouse B16F10 melanoma and CT26-Luciferase colon cancer cells. Both cells were grown in RPMI1640 medium (Sigma, Cat #R6504) supplemented with 10% FBS (Invitrogen, Cat #10438-026), and 1% penicillin streptomycin (Thermo Fisher Scientific, Cat #15140-122). Cell line was harvested by trypsinization when they reached 70-80% confluence. A day before cell inoculation, C57BL/6 mice were maintained under pathogen-free conditions according to SPF guideline (room temperature, 40-60% humidity) and housed in the ABMRC at the Yonsei University. To establish metastasis, B16F10 cells ($1\times10^6$ cells/mouse, n=3/group) were suspended in serum-free media and intravenously injected at tail vein using a 1 mL BD syringe attached to a 24 gauge needle (BD Precision Glide needles, 0.55 mm×25 mm, REF #302805). CT-26-Luciferase cells ($1\times10^4$ cells/mouse, n=5/group) were engrafted at intraperitoneal cavity following 24 hours pretreatment of 30 mg/kg/day of compound 226.

Mice were randomized, and three mice for B16F10 model and five mice for CT26 peritoneal metastasis model were allocated per group. Lung metastasis was measured after 14 days of cell inoculation. Animals were orally administered with vehicle control or the compound 226 (30 mg/kg/day) once a day for the indicated days. Vehicle for oral administration consists of 10% sodium sulphobutylether β-cyclodextrine (SBECD) in 50 mM citrate buffer (pH 3.0). Animals were monitored for mortality and clinical signs (such as illness and behavioral changes) daily throughout the study. In B16F10 model, after mice sacrificed, organs were fixed with 10% of Formalin solution for 1 day. The FFPE block was sliced by 4 μm thinness on coating slides for applying the H&E staining. Then, tumor nodule counting was calculated. CT26 metastasis was determined by measuring luminescence intensity in peritoneal cavity.

Results

Figure 3A:
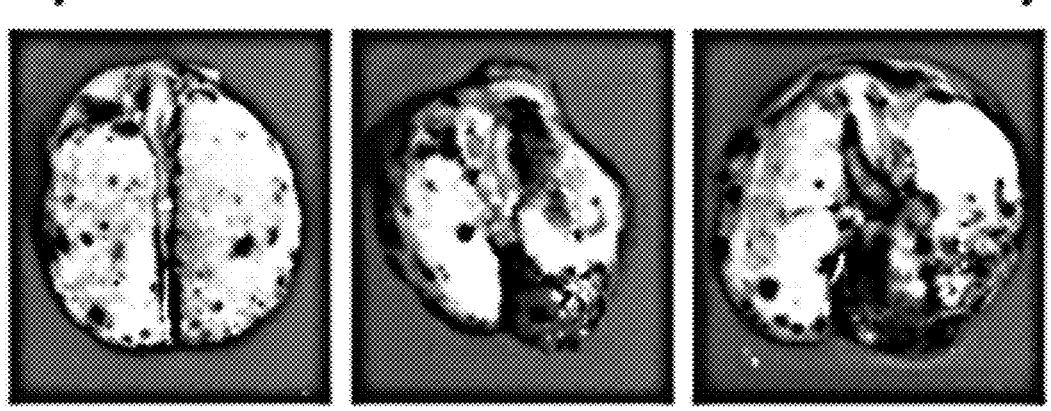
FIGS. 3a to 3c show anti-metastatic activity of compound 226 on B16F10 lung in vivo metastasis model.
Figure 3A:
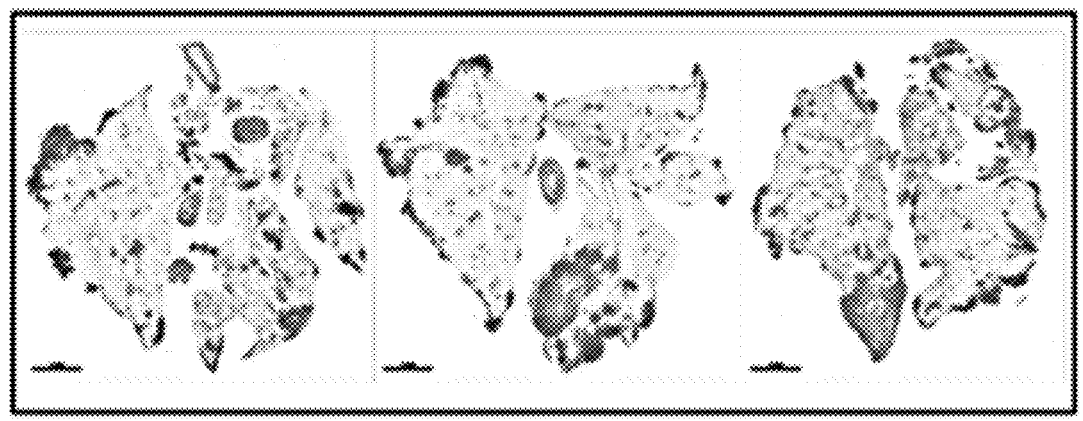
Figure 3B:
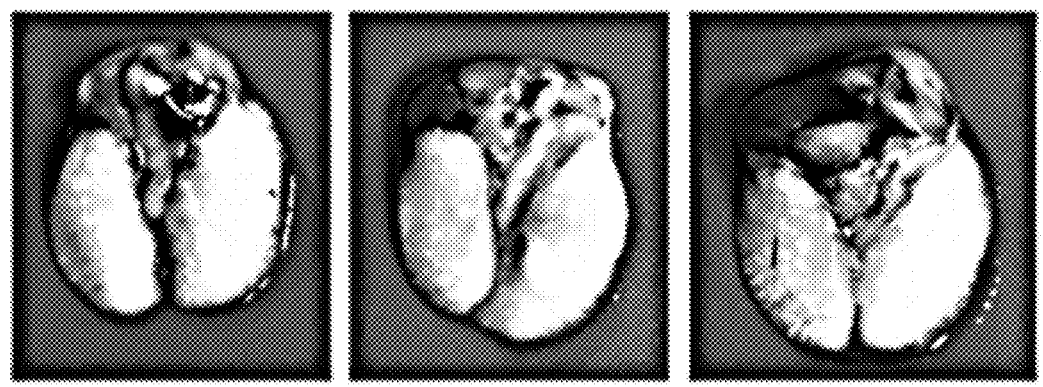
Figure 3B:
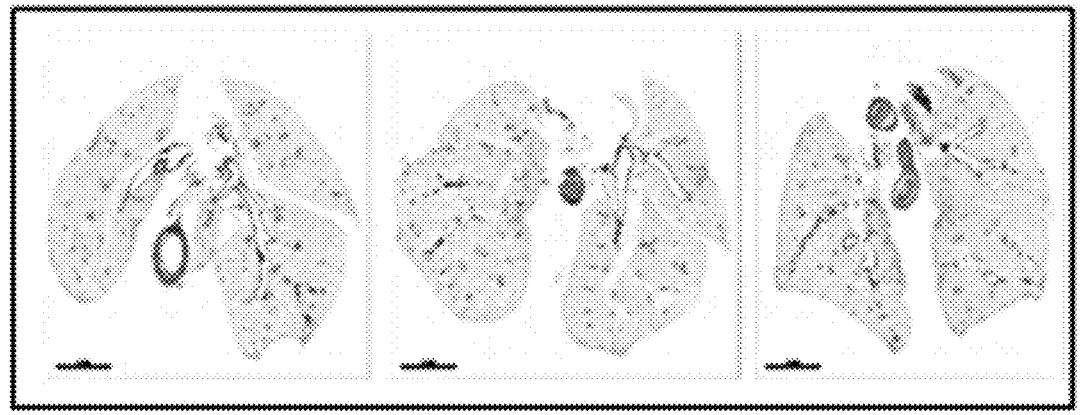
Figure 3C:
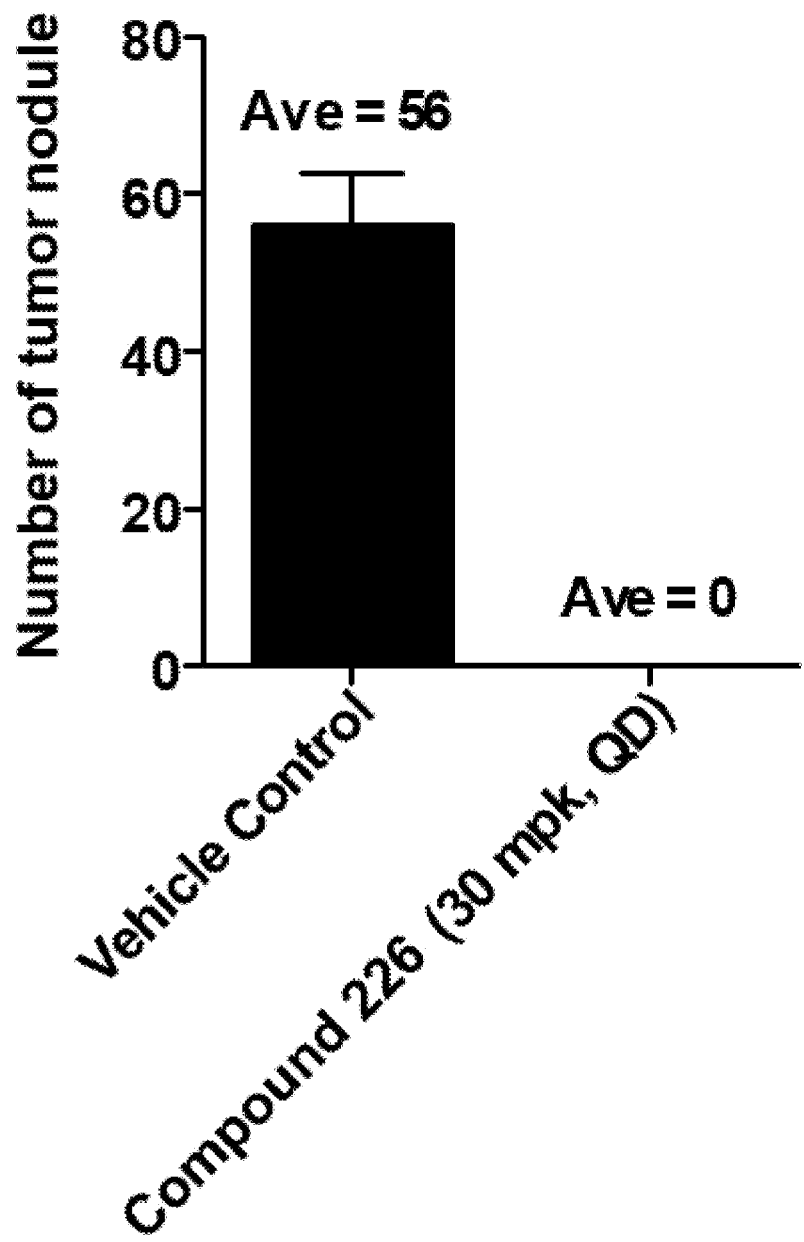
Figure 4A:
FIGS. 4a and 4b show anti-metastatic activity of compound 226 on CT26 peritoneal in vivo metastasis model.
Figure 4A:
Figure 4A:
Figure 4A:
Figure 4A:
Figure 4A:
Figure 4B:
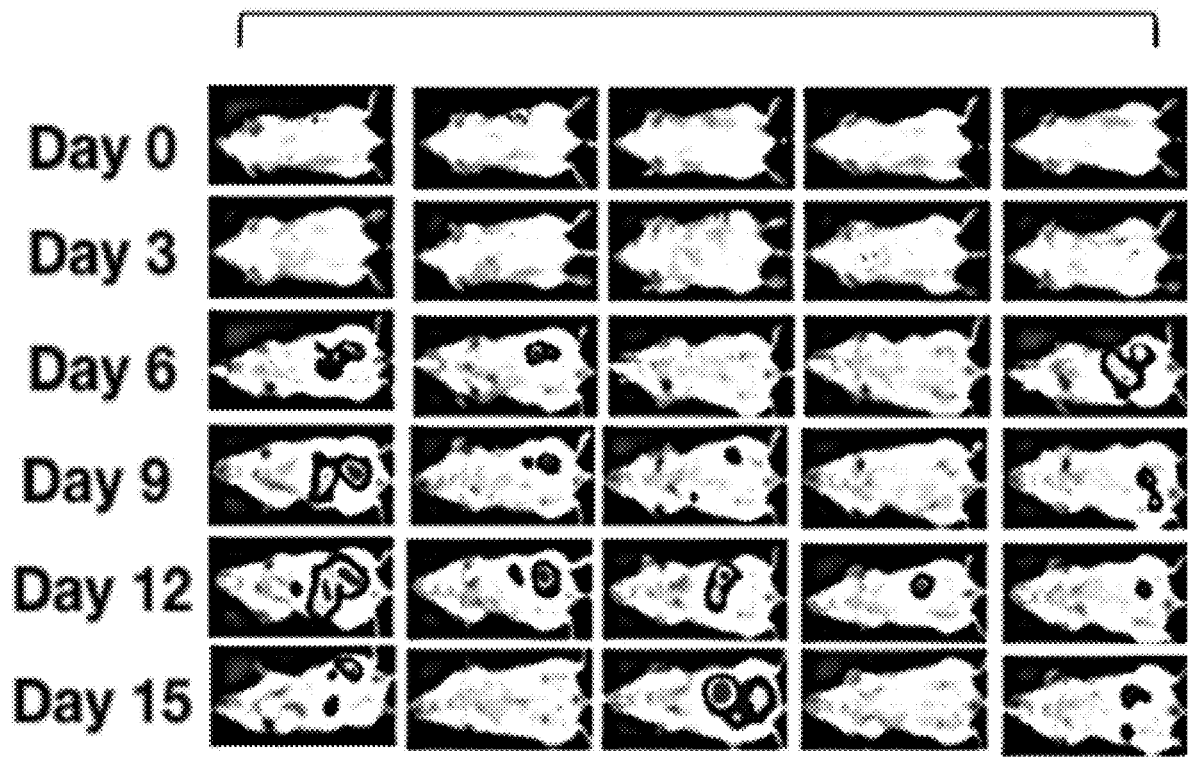

The objective of this study was to evaluate the preventive effect of compound 226 on B16F10 lung and CT-26 peritoneal metastasis models. The treatments of compound 226 were well tolerated as there were no clinical signs of abnormality compared to vehicle control. On day 9, two mice in vehicle group were found dead in CT26 metastasis model. In B16F10 metastasis model, oral 30 mg/kg/day of compound 226 dramatically inhibited lung metastasis in all gross lung specimens shown as black region, and there were no tumor nodules (see FIGS. 3a to 3c). In CT-26 peritoneal metastasis models, compound 226 treatment drastically reduced luminescence intensity in the peritoneal cavity. Additionally, the mice in vehicle group started to die from day 9 after CT26-luciferase cell engraftment, whereas the mice treated with compound 226 (QD, 30 mg/kg/day) were alive during the treatment period (see FIGS. 4a and 4b). Therefore, these results suggest that compound 226 of Formula (I) would be therapeutic potential to prevent metastasis in Axl positive cancer patients.

6. Combination Effect with an Anti-PD-1 Antibody in Metastasis Model

In order to test whether the compounds of Formula (I) show combination effect with mouse anti-PD-1 antibody in 4T1 spontaneous metastasis model, they were tested as follows.

Methods

Compounds of Formula (I) as obtained above were tested in spontaneous metastasis models using mouse 4T1 breast cancer cells. 4T1 cells were grown in RPMI1640 medium (Sigma, Cat #R6504) supplemented with 10% FBS (Invitrogen, Cat #10438-026), and 1% penicillin streptomycin (Thermo Fisher Scientific, Cat #15140-122). Cell line was harvested by trypsinization when they reached 70-80% confluence. A day before cell inoculation, fur on the right flank of BALB/C mice was depilated using hair trimmer. On the following day, the skin area around the injection site was disinfected by mildly swabbing with surgical spirit. To establish allografts, BALB/c female mice (7-weeks age) were implanted orthotopically into the mammary gland with $5 \times 10^6$ syngeneic 4T1 cells. Mice were sacrificed when average tumor volume reached 1500 $mm^3$.

Mice were randomized based on tumor volume (~50 $mm^3$) and five mice were allocated per group. Tumor grafts were measured after approximately 2 days of cell inoculation when they become palpable. Animals were orally administrated with vehicle control or the compound 226 of Formula (I) (30 mg/kg/day) and/or anti-mouse PD-1 antibody for the indicated days. Vehicle for oral administration consists of 10% sodium sulphobutylether β-cyclodextrine (SBECD) in 50 mM citrate buffer (pH 3.0). Animals were monitored for mortality and clinical signs (such as illness and behavioral changes) daily throughout the study. After treatment for 28 days, all mice were sacrificed. 4T1 lung metastasis was determined by counting the tumor nodules through H&E staining. 4T1 solid tumor on primary site was measured by a tumor 3D scanner, TM900 (Peria, Belgium). Mice lung was collected and fixed with 10% of Formalin solution for 24 hours. The FFPE block was sliced by 4 μm thinness on coating slides for applying the H&E staining. The metastatic nodule was measured by microscopic observation.

Results

Figure 5A:
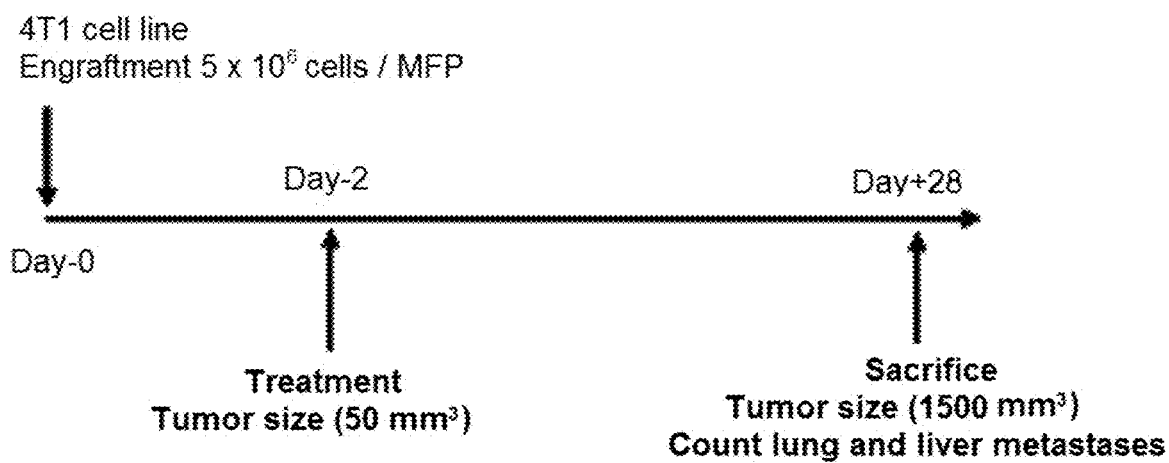
FIG. 5a shows 4T1 spontaneous metastasis model.
Figure 5B:
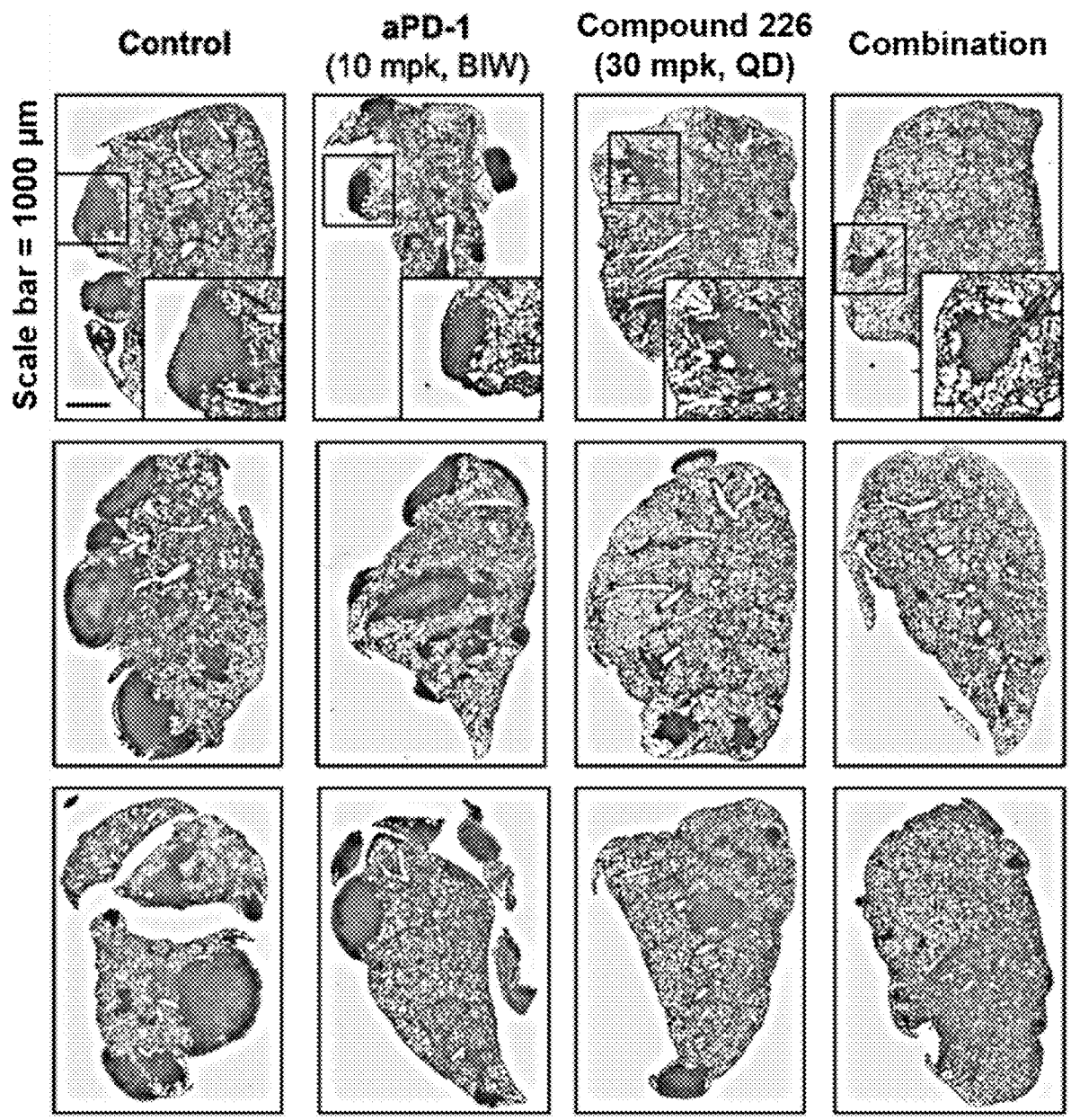
FIGS. 5b and 5c show combination effect with anti-PD-1 antibody on 4T1 orthotropic metastasis model.
Figure 5C:
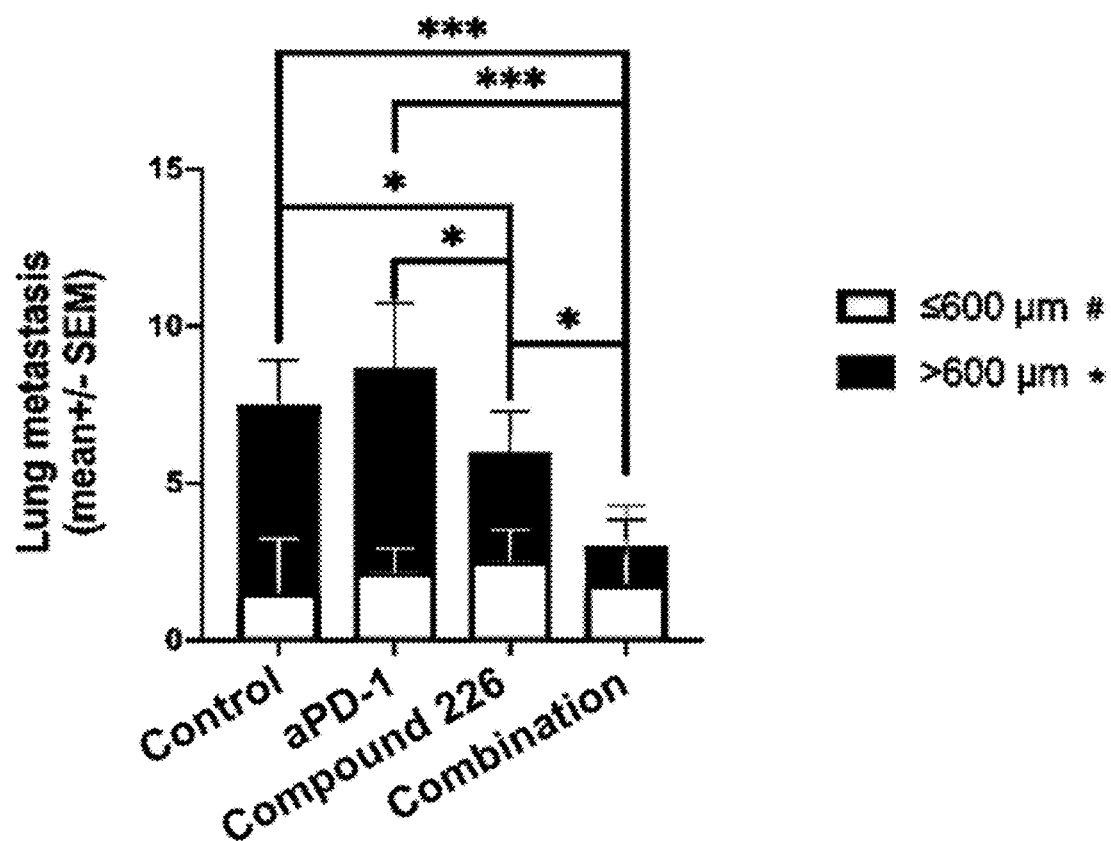
Figure 6:
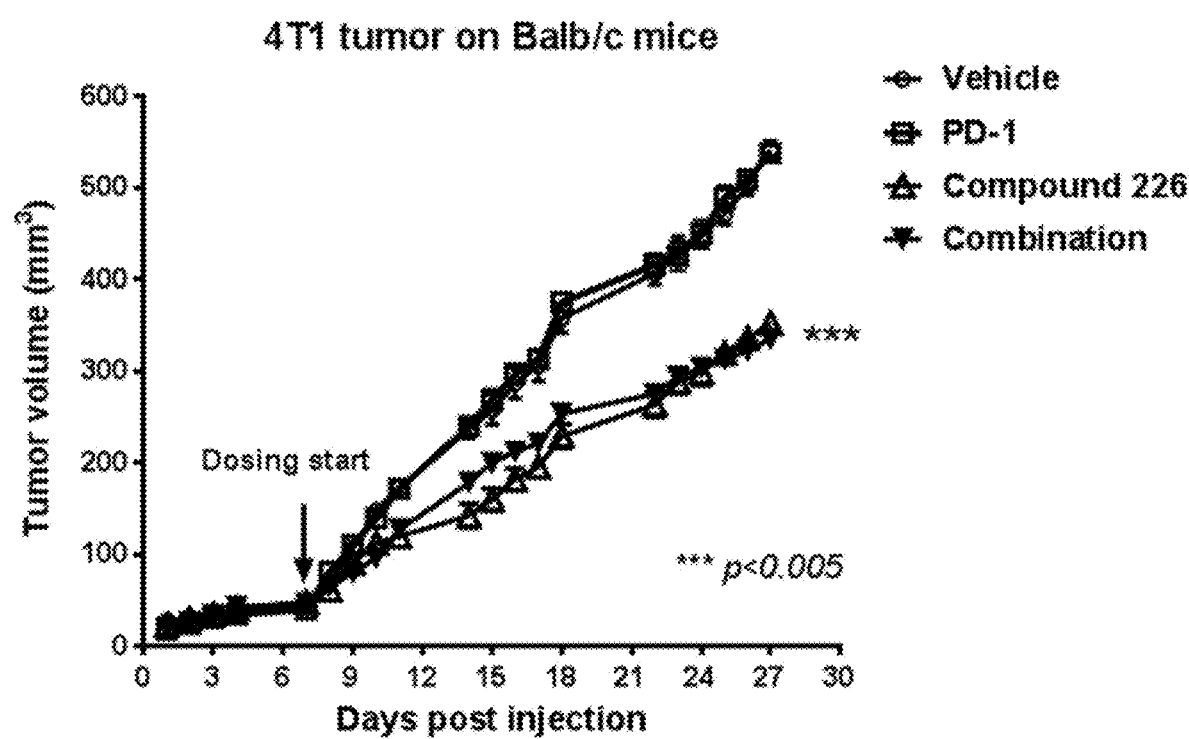
FIG. 6 shows inhibition of tumor growth on primary site (mammary fat pad) in 4T1 orthotropic metastasis model.

BALB/c female mice (7-weeks age) were implanted orthotopically into the mammary gland with $5 \times 10^6$ syngeneic 4T1 cells. When tumors reached a size of approximately 50 $mm^3$, mice were either treated with vehicle, anti-PD-1 antibody (100 mg twice/week), compound 226 of Formula (I) (30 mg/kg/day) or a combination of compound 226 of Formula (I) and anti-PD-1 antibody for 4 weeks. Mice were sacrificed on day 28 and lung metastasis was evaluated by counting nodules. Metastasis into the lung was significantly decreased by compound 226 alone, and the combination with anti-PD1 antibody and compound 226 enhanced the higher reduction of tumor nodules compared to compound 226 treatment alone (see FIGS. 5a to 5c). Anti-PD-1 antibody treated group did not display remarkable efficacy against lung metastasis. Compound 226 significantly suppressed both total metastatic burden and the number of larger metastases (medium+large metastases, ≥5 mm diameter; see FIG. 5c). Regarding to tumor growth on primary site, compound 226 alone and combination groups showed the inhibition of tumor growth which there was no different efficacy between groups, suggesting that the combinational effect would be play on metastatic tumor, not primary tumor (see FIG. 6). Taken together, these results suggest that compound 226 of Formula (I) shows a high potential for immune-oncology application in metastasis treatment.

The invention claimed is:

1. A method of inhibiting Axl in a subject in need thereof, comprising administering an effective amount of a composition comprising 8-bromo-2-((1-methylpiperidin-4-yl)amino)-4-((4-phenoxyphenyl)amino)pyrido[4,3-d]pyrimidin-5(6H)-one hydrochloride, or a pharmaceutically acceptable salt thereof to the subject,
wherein the subject suffers from a disease or condition mediated by Axl;
wherein the disease or condition is a solid tumor;
wherein the method further comprises administering an immune checkpoint blocker; and
wherein the immune checkpoint blocker is an anti-PD-1 antibody.

2. The method of claim 1, wherein the compound of Formula (I) comprises a stereoisomer thereof.

3. The method of claim 1, wherein the disease or condition is adrenocortical carcinoma, aids-related cancers, anal cancer, appendix cancer, astrocytomas, atypical teratoid/rhabdoid tumor, basal cell carcinoma, bile duct cancer, bladder cancer, bone cancer, osteosarcoma, malignant fibrous histiocytoma, brain stem glioma, brain tumor, central nervous system atypical teratoid/rhabdoid tumor, astrocytomas, craniopharyngioma, ependymoblastoma, ependymoma, medulloblastoma, medulloepithelioma, pineal parenchymal tumors of intermediate differentiation, supratentorial primitive neuroectodermal tumors, pineoblastoma, brain and spinal cord tumors, breast cancer, bronchial tumors, burkitt lymphoma, carcinoid tumor, gastrointestinal cancer, central nervous system lymphoma, cervical cancer, chordoma, chronic myeloproliferative disorders, colon cancer, colorectal cancer, craniopharyngioma, mycosis fungoides, endometrial cancer, ependymoblastoma, ependymoma, esophageal cancer, esthesioneuroblastoma, ewing sarcoma family of tumors, extracranial germ cell tumor, extragonadal germ cell tumor, extrahepatic bile duct cancer, intraocular melanoma, retinoblastoma, gallbladder cancer, gastric cancer, gastrointestinal carcinoid tumor, gastrointestinal stromal tumor, gastrointestinal stromal cell tumor, extracranial germ cell tumor, extragonadal germ cell tumor, ovarian germ cell tumor, gestational trophoblastic tumor, glioma, head and neck cancer, heart cancer, hepatocellular cancer, hypopharyngeal cancer, intraocular melanoma, islet cell tumors, kaposi sarcoma, renal cell cancer, kidney cancer, laryngeal cancer, lip and oral cavity cancer, liver cancer, lung cancer, non-small cell lung cancer, small cell lung cancer, malignant fibrous histiocytoma of bone, osteosarcoma, medulloblastoma, medulloepithelioma, melanoma, intraocular melanoma, merkel cell carcinoma, mesothelioma, metastatic squamous neck cancer with occult primary, mouth cancer, multiple endocrine neoplasia syndromes, plasma cell neoplasm, myelodysplastic syndromes, myelodysplastic/myeloproliferative neoplasms, nasal cavity and paranasal sinus cancer, nasopharyngeal cancer, neuroblastoma, non-small cell lung cancer, oral cancer, oral cavity cancer, oropharyngeal cancer, osteosarcoma, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineoblastoma, supratentorial primitive neuroectodermal tumors, pituitary tumor, pleuropulmonary blastoma, pregnancy-related breast cancer, prostate cancer, rectal cancer, renal cell cancer, transitional cell cancer, respiratory tract cancer, retinoblastoma, rhabdomyosarcoma, salivary gland cancer, sarcoma, ewing sarcoma, kaposi sarcoma, uterine sarcoma, nonmelanoma skin cancer, melanoma skin cancer, skin carcinoma, small cell lung cancer, small intestine cancer, soft tissue sarcoma, squamous cell carcinoma, squamous neck cancer, stomach cancer, supratentorial primitive neuroectodermal tumors, testicular cancer, throat cancer, thymoma, thymic carcinoma, thyroid cancer, transitional cell cancer of renal pelvis and ureter, trophoblastic tumor, gestational cancer, ureter and renal pelvis cancer, transitional cell cancer, urethral cancer, uterine cancer, endometrial cancer, uterine sarcoma, vaginal cancer, vulvar cancer, Waldenstrom macroglobulinemia, or Wilms tumor.

4. The method of claim 1, wherein the composition further comprises a pharmaceutically acceptable carrier, diluent, adjuvant, or excipient.

5. The method of claim 1, wherein the subject has received or is undergoing chemotherapy and/or radiation therapy.

* * * * *